(12) United States Patent
El Sayed et al.

(10) Patent No.: US 8,969,303 B2
(45) Date of Patent: Mar. 3, 2015

(54) TOCOTRIENOL ESTERS

(75) Inventors: Khalid A. El Sayed, West Monroe, LA (US); Paul W. Sylvester, West Monroe, LA (US)

(73) Assignee: First Tech International Limited, Hong Kong (CN)

( * ) Notice: Subject to any disclaimer, the term of this patent is extended or adjusted under 35 U.S.C. 154(b) by 349 days.

(21) Appl. No.: 13/021,361

(22) Filed: Feb. 4, 2011

(65) Prior Publication Data
US 2011/0196030 A1    Aug. 11, 2011

Related U.S. Application Data

(60) Provisional application No. 61/301,665, filed on Feb. 5, 2010.

(51) Int. Cl.
| | | |
|---|---|---|
| *A01N 43/16* | (2006.01) | |
| *A61K 31/355* | (2006.01) | |
| *A61K 38/00* | (2006.01) | |
| *A61P 35/00* | (2006.01) | |
| *C07D 311/72* | (2006.01) | |
| *A61K 31/19* | (2006.01) | |
| *A61K 31/192* | (2006.01) | |

(52) U.S. Cl.
CPC .............. *C07D 311/72* (2013.01); *A61K 31/19* (2013.01); *A61K 31/192* (2013.01); *A61K 31/355* (2013.01)
USPC ........................................ 514/19.3; 514/458

(58) Field of Classification Search
None
See application file for complete search history.

(56) References Cited

U.S. PATENT DOCUMENTS

| | | | |
|---|---|---|---|
| 4,595,783 | A | 6/1986 | Vogel et al. |
| 5,393,776 | A | 2/1995 | Pearce |
| 5,591,772 | A | 1/1997 | Lane |
| 5,670,668 | A | 9/1997 | Hyatt |
| 5,869,704 | A | 2/1999 | Hyatt |
| 6,043,269 | A | 3/2000 | Jacobsen et al. |
| 6,136,851 | A | 10/2000 | Bonte et al. |
| 6,387,882 | B1 | 5/2002 | Ogata |
| 6,441,029 | B1 | 8/2002 | Elson |
| 2007/0207196 | A1 | 9/2007 | Zhang |

FOREIGN PATENT DOCUMENTS

| | | |
|---|---|---|
| WO | 0059492 A2 | 10/2000 |
| WO | WO03/039461 | 5/2003 |
| WO | WO2006094791 | 9/2006 |

OTHER PUBLICATIONS

Shirode et. al., Synergistic anticancer effects of combined g-tocotrienol and celecoxib treatment are associated with suppression in Akt and NFkB signaling Biomedicine & Pharmacotherapy, Nov. 14, 2009, pp. 327-332, vol. 64, Elsevier.
Shirode et. al., Mechanisms Mediating the Synergistic Anticancer Effects of Combined γ-Tocotrienol and Celecoxib Treatment J. Bioanalysis & Biomedicine 2011, pp. 7—Jan., vol. 3(1).
Pearce et al., Inhibitors of Cholesterol Biosynthesis Hypocholesterolemic and Antioxidant Activities of Benzopyran and Tetrahydronaphthalene Analogues of the Tocotrienols Journal of Medicinal Chemistry, 1994, pp. 526-541, vol. 37, No. 4, American Chemical Society.
McIntyre et al. Antiproliferative and Apoptotic Effects of Tocopherols and Tocotrienols on Preneoplastic and Neoplastic Mouse Mammary Epithelial Cells Society for Experimental Biology and Medicine, 2000, pp. 292-301, vol. 224.
Sylvester et al., Role of Tocotrienols in the Prevention of Cardiovascular Disease and Breast Cancer Current Topics in Nutraceutical Research, 2003, pp. 1-16 vol. 1(2).
Shah et al., Tocotrienol-Induced Caspase-8 Activation Is Not Associated with Death Receptor Apoptotic Signaling in Neoplastic Mammary Epithelial Cells Society for Experimental Biology and Medicine, 2004 p. 229.
Shah et al., γ-Tocotrienol Inhibits Neoplastic Mammary Epithelial Cell Proliferation by Decreasing Akt and Nuclear Factor κB, Activity Society for Experimental Biology and Medicine, 2005, pp. 235-241.
Shah et al., Tocotrienol-induced cytotoxicity is unrelated to mitochondrial stress apoptotic signaling in neoplastic mammary epithelial cells, Biochem. Cell Biol., 2005, pp. 86-95, vol. 83.
Matter et al., Structural Requirements for Factor Xa Inhibition by 3-Oxybenzamides with Neutral P1 Substituents: Combining X-ray Crystallography, 3D-QSAR and Tailored Scoring Functions, Journal of Medical Chemistry, Apr. 13, 2005, pp. 3290-3312, vol. 25 American Chemical Society.
Samant et al., γ-Tocotrienol inhibits ErbB3-dependent PI3K/Akt mitogenic signalling in neoplastic mammary epithelial cells Cell Proliferation, 2006, pp. 563-574, vol. 39, Blackwell Publishing Ltd.
Sylvester, Vitamin E and Apoptosis Vitamins and Hormones, 2007, pp. 329-356, vol. 76, Elsevier, Inc.
Kashiwagi et al., A redox-silent analogue of tocotrienol inhibits hypoxic adaption of lung cancer cells, Biochemical and Biophysical Research Communication, Nov. 8, 2007, pp. 875-881, vol. 365, Elsevier, Inc.
Constantinou et al., Vitamin E and cancer: An insight into the anticancer activities of vitamin E isomers and analogs, International Journal of Cancer, May 29, 2008, pp. 739-752, vol. 123, Wiley-Liss, Inc.
Chang et al., Evidence of γ-Tocotrienol as an Apoptosis-Inducing, Invastion-Suppressing, and Chemotherapy Drug-Sensitizing Agent in Human Melanoma Cells Nutrition and Cancer, Nutrition and Cancer, 2009, pp. 357-366, vol. 61 (3).
Wali et al., Combined Treatment of c-Tocotrienol with Statins Induce Mammary Tumor Cell Cycle Arrest in G1, Society for Experimental Biology and Medicine, 2009, pp. 639-650.
Ali et al., Development and validation of a reversed-phase HPLC method for the simultaneous analysis of simvastatin and tocotrienols in combined dosage forms, Journal of Pharmaceutical and Biomedical Analysis, Feb. 20, 2009, pp. 950-956, vol. 49 2009, Elsevier, Inc.

(Continued)

*Primary Examiner* — Anna Pagonakis
(74) *Attorney, Agent, or Firm* — John B. Edel; Edel Patents LLC

(57) ABSTRACT

Esters of tocotrienols having pharmacological activities pertinent to the treatment of breast cancer and other forms of cancer are disclosed herein. Among those compounds is (Z)-4-oxo-4-((R)-2,5,7,8-tetramethyl-2-((3E,7E)-4,8,12-trimethyltrideca-3,7,11-trienyl)chroman-6-yloxy)but-2-enoic acid. Tocotrienol esters were used to inhibit the growth and migration of +SA mammary epithelial cells and highly metastatic human breast cancer MDA-MB-231 cells respectively.

28 Claims, 21 Drawing Sheets

(56) References Cited

OTHER PUBLICATIONS

Wali et al., Endoplasmic reticulum stress mediates c-tocotrienol-induced apoptosis in mammary tumor cells, Apoptosis, Sep. 23, 2009, pp. 1366-1377, vol. 14.

Elnagar et al., Design and preliminary structure—activity relationship of redox-silent semisynthetic tocotrienol analogues as inhibitors for breast cancer proliferation and invasion, Bioorganic & Medicinal Chemistry, Nov. 27, 2009, pp. 755-768, vol. 18, Elsevier, Inc.

Gupte et al., CoMFA and CoMSIA 3D-QSAR Studies on S6-(4-nitrobenzyl)mercaptopurine riboside (NBMPR) analogs as inhibitors of human equilibrative nucleoside transporter 1 (Hent1), Bioorganic & Medicinal Chemistry Letters, 2009, pp. 314-318, vol. 19, Elsevier, Inc.

Abuasal et al., Intestinal Absorption of γ-Tocotrienol Is Mediated by Niemann-Pick C1-Like 1: In Situ Rat Intestinal Perfusion Studies, Drug Metabolism and Disposition, 2010, pp. 939-945, vol. 38(6).

Aggarwal et al., Tocotrienols, the vitamin E of the 21st century: Its potential against cancer and other chronic diseases, Biochemical Pharmacology, 2010, pp. 1-19, vol. 10676, Elsevier, Inc.

Bachawal et al., Enhanced antiproliferative and apoptotic response to combined treatment of g-tocotrienol with erlotinib or gefitinib in mammary tumor cells, BMC Cancer, 2010, pp. 1-13, vol. 10:14.

Bachawal et al., Combined γ-Tocotrienol and Erlotinib/Gefitinib Treatment Suppresses Stat and Akt Signaling in Murine Mammary Tumor Cells, Anticancer Research, 2010, pp. 429-438, vol. 30.

MUDIT Synthesis of Fluorescent Analogues of the Anticancer Natural Products 4-Hydroxyphenylmethylene Hydantoin and δ-Tocotrienol, Natural Product Communications, 2010, pp. 1623-1626, vol. 5(10), Natural Product Communications, Westerville, Ohio.

Samant et al., Anti-proliferative effects of c-tocotrienol on mammary tumour cells are associated with suppression of cell cycle progression, Cell Proliferation, 2010, pp. 77-83, vol. 43, Blackwell Publishing Ltd.

Sylvester et al., The Value of Tocotrienols in the Prevention and Treatment of Cancer, Journal of the American College of Nutrition, 2010, pp. 324S-333S, vol. 29(3), American College of Nutrition.

El Sayed et al., Biocatalytic and semisynthetic optimization of the anti-invasive tobacco (1S,2E,4R,6R,7E,11E)-2,7,11-cembratriene-4,6-diol, Bioorganic & Medicinal Chemistry, Jan. 3, 2008, pp. 8066-8075, vol. 18, Elsevier, Inc.

Ali et al., Preparation, characterization, and anticancer effects of simvastatin—tocotrienol lipid nanoparticles, International Journal of Pharmaceuticals, Feb. 10, 2010, pp. 233-231, vol. 389, Elsevier, Inc.

Ali et al., Molecular interaction and localization of tocotrienol-rich fraction (TRF) within the matrices of lipid nanoparticles: Evidence studies by Differential Scanning Calorimetry (DSC) and Proton Nuclear Magnetic Resonance spectroscopy (1H NMR) Colloids and Surfaces B:, Biointerfaces, 2010, pp. 286-297, vol. 77, Elsevier, Inc.

Behery et al., Redox-silent tocotrienol esters as breast cancer proliferation and migration inhibitors, Bioorganic & Medicinal Chemistry, 2010, pp. 8069-8075, vol. 18, Elsevier, Inc.

Ali et al., Preparation, characterization, and anticancer effects of simvastatin—tocotrienol lipid nanoparticles Colloids and Surfaces A: Physiochem. Eng., Aspects, Oct. 30, 2009, pp. 43-51, vol. 353, Elsevier, Inc.

Sen, et al., Journal of Biol Chem, 2000, pp. 13049, vol. 275.
Crowell, et al., Journal Biol Chem, 1991, pp. 17679, vol. 266.
Elson, et al., Journal Nutr., 1994, pp. 607, vol. 124.
Sporn, et al., Nat. Rev. Cancer, 2002, pp. 537, vol. 2.
Shukla, et al., Nutr. Cancer, 2005, pp. 18, vol. 53.
Nesaretnam, et al., Lipids, 1995, pp. 1139, vol. 30.
Qureshi, et al., Atherosclerosis, 2002, pp. 199, vol. 161.
Khanna, et al., Journal of Biol Chem, 2003, pp. 43508, vol. 278.
Akaho, et al., Drug Metab. Dispos., 2007, pp. 1502, vol. 35.
Takata, et al., Journal Lipid Res, 2002, pp. 2196, vol. 43.
Search Results from search of American Chemical Society SciFinder database run in Jul. 2012 (1 of 4).
Search Results from search of American Chemical Society SciFinder database run in Jul. 2012 (2 of 4).
Search Results from search of American Chemical Society SciFinder database run in Jul. 2012 (3 of 4).
Search Results from search of American Chemical Society SciFinder database run in Jul. 2012 (4 of 4).
Mazzini, et al., Journal Org. Chem, 2009, pp. 2063, vol. 13.
Tomic-Vatic, et. al., Int. J. Cancer, 2005, pp. 188, vol. 117.
Kashiwagi, et al., Biochem, Biophys. Res. Commun., 2008, pp. 875, vol. 365.
Ali, et al., Pharm Biomed. Anal., 2009, pp. 950, vol. 49.
Chang, et al., Nutr. Cancer, 2009, pp. 357, vol. 61.
Yap, et al., Br. J. Cancer, 2008, pp. 1832, vol. 99.
Tamilarasan, et al., Cell Biol., 2006, pp. 17, vol. 7.
Borghesani,, et al., Development, 2002, pp. 1435, vol. 6.
Kubinyi, et al., Burger's Medicinal Chemistry, 1995, pp. 497-571, vol. 1.
Denizot, et al., Immunol, Methods, 1986, pp. 271, vol. 89.
Kleinman, et al., Cancer Biol., 2005, pp. 378, vol. 15.
Koblinski, et al., Cancer Res., 2005, pp. 7370, vol. 65.
El Sayed et al., Latrunculin A and Its C-17-0 Carbamates Inhibit Prostate Tumor Cell Invasion and HIF-1 Activation in Breast Tumor Cells, Journal of Natural Products, 2008, pp. 396-402, vol. 71.

Arya et al., Design and synthesis of analogs of Vitamin E: Antiproliferative activity against human breast adenocarcinoma cells, Bioorganic Medicinal Chemistry Letters, Sep. 22, 1998, pp. 2433-2438, vol. 8(18).

McIntyre et al., Antiproliferative and Apoptotic Effects of Tocopherols and Tocotrienols on Normal Mouse and Mammary Epithelial Cells Lipids, 2000, pp. 171-180, vol. 35(2), AOCS Press.

Shah et al., Role of Caspase-8 Activation in Mediating Vitamin E-Induced Apoptosis in Murine Mammary Cancer Cells, Nutrition and Cancer, 2003, pp. 236-246, vol. 45(2), Lawrence Erlbaum Associates, Inc.

Liua et al., Inhibitory Effects of γ-tocotrienol on invastion and metastasis of human gastric denocarcinoma SGC-7901 Cells, Journal of Nutritional Biology, Feb. 5, 2009, vol. 11, Elsevier, Inc.

Supplementary European search report for related application, Application No. EP 11740426, May 23, 2013.

International Search Report for related application, Application No. PCT/US11/23748, Jun. 9, 2011.

| Compound | $R_1$ | $R_2$ | $R_3$ |
|---|---|---|---|
| 1 | $CH_3$ | a | $CH_3$ |
| 2 | H | a | $CH_3$ |
| 3 | $CH_3$ | b | $CH_3$ |
| 4 | H | b | $CH_3$ |
| 5 | H | b | H |
| 6 | $CH_3$ | c | $CH_3$ |
| 7 | H | c | $CH_3$ |
| 8 | H | c | H |
| 9 | H | d | $CH_3$ |
| 10 | H | e | $CH_3$ |
| 11 | H | f | $CH_3$ |
| 12 | H | g | $CH_3$ |
| 13 | H | h | $CH_3$ |
| 14 | H | i | $CH_3$ |

Fig. 3

| | Compound 1 | | Compound 2 | |
|---|---|---|---|---|
| position | $\delta_C$, mult. | $\delta_H$ (J in Hz) | $\delta_C$, mult. | $\delta_H$ (J in Hz) |
| 2 | 75.0, qC | | 76.8, qC | |
| 2-CH$_3$ | 17.7, CH$_3$ | 1.22, s | 24.1, CH$_3$ | 1.26, s |
| 3 | 31.2, CH$_2$ | 1.76, m | 31.1, CH$_2$ | 1.76, m |
| 4 | 20.7, CH$_2$ | 2.59, m | 22.3, CH$_2$ | 2.74, m |
| 5 | 123.3, CH | | 118.6, CH | 6.81, s |
| 5-CH$_3$ | 11.9, CH$_3$ | 2.05, s | | |
| 6 | 149.7, qC | | 150.0, qC | |
| 7 | 125.4, qC | | 127.2, qC | |
| 7-CH$_3$ | 13.1, CH$_3$ | 2.09, s | 12.1, CH$_3$ | 2.13, s |
| 8 | 127.1, qC | | 126.1, qC | |
| 8-CH$_3$ | 12.2, CH$_3$ | 2.08, s | 12.8, CH$_3$ | 2.12, s |
| 9 | 117.6, qC | | 118.8, qC | |
| 10 | 140.6, qC | | 141.6, qC | |
| 1' | 39.8, CH$_2$ | 1.53, 1.60, m | 39.8, CH$_2$ | 1.56, 1.64, m |
| 2' | 22.2, CH$_2$ | 2.07, 2.14, m | 22.3, CH$_2$ | 2.11, 2.15, m |
| 3' | 124.4, CH | 5.06, m | 124.5, CH | 5.09, m |
| 4' | 135.0, qC | | 135.3, qC | |
| 4'-CH$_3$ | 15.9, CH$_3$ | 1.55, s | 16.0, CH$_3$ | 1.58, s |
| 5' | 39.8, CH$_2$ | 1.94, m | 39.8, CH$_2$ | 1.96, m |
| 6' | 26.8, CH$_2$ | 2.02, m | 26.8, CH$_2$ | 2.06, m |
| 7' | 124.2, CH | 5.06, m | 124.3, CH | 5.09, m |
| 8' | 134.9, qC | | 135.1, qC | |
| 8'-CH$_3$ | 16.0, CH$_3$ | 1.55, s | 16.1, CH$_3$ | 1.58, s |
| 9' | 39.8, CH$_2$ | 1.94, m | 39.8, CH$_2$ | 1.96, m |
| 10' | 26.6, CH$_2$ | 2.02, m | 26.7, CH$_2$ | 2.06, m |
| 11' | 124.3, CH | 5.06, m | 124.3, CH | 5.09, m |
| 12' | 131.4, qC | | 130.5, qC | |
| 12'a-CH$_3$ | 16.6, CH$_3$ | 1.57, s | 17.8, CH$_3$ | 1.60, s |
| 12'b-CH$_3$ | 25.7, CH$_3$ | 1.63, s | 25.8, CH$_3$ | 1.66, s |
| 1" | 169.1, qC | | 170.4, qC | |
| 2" | 133.8, qC | | 131.8, qC | |
| 3" | 135.3, qC | | 138.0, qC | |
| 3"-COO | 165.6, qC | | 166.6, qC | |
| 4" | 129.4, CH | 8.03, d (8.04) | 129.2, CH | 7.92, d (8.04) |
| 5" | 132.2, CH | 8.23, dd (1.84, 8.08) | 133.9, CH | 8.37, dd (1.48, 8.04) |
| 6" | 133.5, qC | | 131.3, qC | |
| 6"-COO | 167.2, qC | | 169.6, qC | |
| 7" | 130.7, CH | 8.44, d, (1.44) | 131.0, CH | 8.71, d (1.44) |

Fig. 9

| | Compound 3 | | Compound 4 | |
| --- | --- | --- | --- | --- |
| position | $\delta_C$, mult. | $\delta_H$ ($J$ in Hz) | $\delta_C$, mult. | $\delta_H$ ($J$ in Hz) |
| 2 | 75.0, qC | | 75.9, qC | |
| 2-CH$_3$ | 17.8, CH$_3$ | 1.26, s | 24.1, CH$_3$ | 1.24, s |
| 3 | 31.2, CH$_2$ | 1.80, m | 31.1, CH$_2$ | 1.74, m |
| 4 | 22.3, CH$_2$ | 2.61, m | 22.2, CH$_2$ | 2.71, m |
| 5 | 123.3, CH | | 118.7, CH | 6.76, s |
| 5-CH$_3$ | 12.0, CH$_3$ | 2.05, s | --- | |
| 6 | 149.7, qC | | 149.8, qC | |
| 7 | 125.3, qC | | 127.4, qC | |
| 7-CH$_3$ | 13.1, CH$_3$ | 2.12, s | 12.0, CH$_3$ | 2.10, s |
| 8 | 127.0, qC | | 126.0, qC | |
| 8-CH$_3$ | 12.3, CH$_3$ | 2.10, s | 12.7, CH$_3$ | 2.07, s |
| 9 | 117.6, qC | | 118.6, qC | |
| 10 | 140.6, qC | | 141.7, qC | |
| 1' | 39.8, CH$_2$ | 1.57, 1.62, m | 39.8, CH$_2$ | 1.50, 1.57, m |
| 2' | 20.7, CH$_2$ | 2.07, 2.14, m | 22.3, CH$_2$ | 2.04, 2.08, m |
| 3' | 124.5, CH | 5.09, m | 124.4, CH | 5.07, m |
| 4' | 135.3, qC | | 135.3, qC | |
| 4'-CH$_3$ | 16.0, CH$_3$ | 1.58, s | 15.9, CH$_3$ | 1.55, s |
| 5' | 39.8, CH$_2$ | 1.96, m | 39.8, CH$_2$ | 1.93, m |
| 6' | 26.8, CH$_2$ | 2.04, m | 26.8, CH$_2$ | 2.01, m |
| 7' | 124.3, CH | 5.09, m | 124.2, CH | 5.07, m |
| 8' | 135.1, qC | | 135.1, qC | |
| 8'-CH$_3$ | 16.1, CH$_3$ | 1.58, s | 16.0, CH$_3$ | 1.55, s |
| 9' | 39.8, CH$_2$ | 1.96, m | 39.8, CH$_2$ | 1.93, m |
| 10' | 26.7, CH$_2$ | 2.04, m | 26.6, CH$_2$ | 2.01, m |
| 11' | 124.3, CH | 5.09, m | 124.2, CH | 5.07, m |
| 12' | 130.4, qC | | 131.4, qC | |
| 12'a-CH$_3$ | 16.5, CH$_3$ | 1.60, s | 17.7, CH$_3$ | 1.57, s |
| 12'b-CH$_3$ | 25.8, CH$_3$ | 1.66, s | 25.7, CH$_3$ | 1.63, s |
| 1" | 169.7, qC | | 168.8, qC | |
| 2" | 138.3, qC | | 136.5, qC | |
| 3" | 132.4, qC | | 133.1, qC | |
| 3"-COO | 164.8, qC | | 166.4, qC | |
| 4" | 131.2, CH | 8.75, d (1.48) | 130.4, CH | 8.51, d (1.48) |
| 5" | 131.4, qC | | 134.3, qC | |
| 5"-COO | 167.3, qC | | 167.1, qC | |
| 6" | 133.4, CH | 8.29, dd (1.48, 8.04) | 132.7, CH | 8.21, dd (1.48, 7.72) |
| 7" | 129.1, CH | 7.81, d (8.08) | 129.5, CH | 7.86, d (8.04) |

Fig. 10

| | Compound 5 | | Compound 6 | |
|---|---|---|---|---|
| position | $\delta_C$, mult. | $\delta_H$ ($J$ in Hz) | $\delta_C$, mult. | $\delta_H$ ($J$ in Hz) |
| 2 | 76.0, qC | | 75.0, qC | --- |
| 2-CH$_3$ | 24.1, CH$_3$ | 1.24, s | 24.2, CH$_3$ | 1.25, s |
| 3 | 31.1, CH$_2$ | 1.75, m | 31.1, CH$_2$ | 1.76, m |
| 4 | 22.5, CH$_2$ | 2.73, m | 20.7, CH$_2$ | 2.60, m |
| 5 | 119.0, CH | 6.77, d (2.92) | 123.3, qC | |
| 5-CH$_3$ | | | 11.9, CH$_3$ | 1.96, s |
| 6 | 150.0, qC | | 149.8, qC | |
| 7 | 121.0, CH | 6.82, d (2.56) | 124.8, qC | |
| 7-CH$_3$ | | | 13.1, CH$_3$ | 2.10, s |
| 8 | 127.5, qC | | 126.6, qC | |
| 8-CH$_3$ | 16.1, CH$_3$ | 2.13, s | 12.2, CH$_3$ | 2.00, s |
| 9 | 121.1, qC | | 117.6, qC | |
| 10 | 142.6, qC | | 140.3, qC | |
| 1' | 39.8, CH$_2$ | 1.50, 1.59, m | 39.8, CH$_2$ | 1.54, 1.62, m |
| 2' | 22.2, CH$_2$ | 2.06, 2.10, m | 22.3, CH$_2$ | 2.08, m |
| 3' | 124.4, CH | 5.06, m | 124.5, CH | 5.09, m |
| 4' | 135.4, qC | | 135.3, qC | |
| 4'-CH$_3$ | 15.9, CH$_3$ | 1.55, s | 16.1, CH$_3$ | 1.59, s |
| 5' | 39.8, CH$_2$ | 1.92, m | 39.8, CH$_2$ | 1.96, m |
| 6' | 26.8, CH$_2$ | 2.02, m | 26.8, CH$_2$ | 2.05, m |
| 7' | 124.2, CH | 5.06, m | 124.3, CH | 5.09, m |
| 8' | 135.1, qC | | 135.1, qC | |
| 8'-CH$_3$ | 16.0, CH$_3$ | 1.55, s | 16.0, CH$_3$ | 1.59, s |
| 9' | 39.8, CH$_2$ | 1.92, m | 39.8, CH$_2$ | 1.96, m |
| 10' | 26.6, CH$_2$ | 2.02, m | 26.7, CH$_2$ | 2.05, m |
| 11' | 124.2, CH | 5.06, m | 124.3, CH | 5.09, m |
| 12' | 131.4, qC | | 131.3, qC | |
| 12'a-CH$_3$* | 17.7, CH$_3$ | 1.56, s | 17.8, CH$_3$ | 1.58, s |
| 12'b-CH$_3$* | 25.7, CH$_3$ | 1.63, s | 25.8, CH$_3$ | 1.67, s |
| 1" | 166.8, qC | | 163.8, qC | |
| 2" | 136.0, qC | | 133.4, CH | 7.13, d (15.76) |
| 3" | 133.2, qC | | 135.6, CH | 7.06, d (15.76) |
| 3"-COO | 168.6, qC | | | |
| 4" | 130.4, CH | 8.45, d (1.44) | 168.7, qC | |
| 5" | 134.4, qC | | | |
| 5"-COO | 167.1, qC | | | |
| 6" | 133.2, CH | 8.21, dd (1.48, 7.04) | | |
| 7" | 129.5, CH | 7.89, d (8.04) | | |

Fig. 11

|  | Compound 7 | | Compound 8 | |
| --- | --- | --- | --- | --- |
| position | $\delta_C$, mult. | $\delta_H$ ($J$ in Hz) | $\delta_C$, mult. | $\delta_H$ ($J$ in Hz) |
| 2 | 76.8, qC | --- | 76.8, qC | |
| 2-CH$_3$ | 24.2, CH$_3$ | 1.27, s | 24.2, CH$_3$ | 1.27, s |
| 3 | 31.1, CH$_2$ | 1.76, m | 31.0, CH$_2$ | 1.80, m |
| 4 | 22.3, CH$_2$ | 2.71, m | 22.2, CH$_2$ | 2.74, m |
| 5 | 118.7, CH | 6.62, s | 118.8, CH | 6.67, d (2.56) |
| 5-CH$_3$ | --- | | --- | |
| 6 | 149.9, qC | | 142.1, qC | |
| 7 | 126.9, C | | 120.9, CH | 6.72, d (2.2) |
| 7-CH$_3$ | 12.1, CH$_3$ | 2.12, s | --- | |
| 8 | 126.1, qC | | 127.6, qC | |
| 8-CH$_3$ | 12.8, CH$_3$ | 2.02, s | 16.2, CH$_3$ | 2.15, s |
| 9 | 118.5, qC | | 121.1, qC | |
| 10 | 141.4, qC | | 150.1, qC | |
| 1' | 39.8, CH$_2$ | 1.54, 1.62, m | 39.8, CH$_2$ | 1.53, 1.64, m |
| 2' | 22.3, CH$_2$ | 2.09, m | 22.5, CH$_2$ | 2.11, m |
| 3' | 124.5, CH | 5.10, m | 124.5, CH | 5.11, m |
| 4' | 135.3, qC | | 135.4, qC | |
| 4'-CH$_3$ | 16.1, CH$_3$ | 1.59, s | 16.1, CH$_3$ | 1.59, s |
| 5' | 39.8, CH$_2$ | 1.97, m | 39.8, CH$_2$ | 1.96, m |
| 6' | 26.8, CH$_2$ | 2.04, m | 26.8, CH$_2$ | 2.04, m |
| 7' | 124.3, CH | 5.10, m | 124.2, CH | 5.11, m |
| 8' | 135.0, qC | | 135.1, qC | |
| 8'-CH$_3$ | 16.0, CH$_3$ | 1.59, s | 16.0, CH$_3$ | 1.59, s |
| 9' | 39.8, CH$_2$ | 1.97, m | 39.8, CH$_2$ | 1.96, m |
| 10' | 26.7, CH$_2$ | 2.04, m | 26.7, CH$_2$ | 2.04, m |
| 11' | 124.3, CH | 5.10, m | 124.2, CH | 5.11, m |
| 12' | 131.3, qC | | 131.4, qC | |
| 12'a-CH$_3$* | 17.7, CH$_3$ | 1.58, s | 17.8, CH$_3$ | 1.59, s |
| 12'b-CH$_3$* | 25.8, CH$_3$ | 1.67, s | 25.8, CH$_3$ | 1.67, s |
| 1" | 164.1, qC | | 164.0, qC | |
| 2" | 134.2, CH | 7.15, d (15.72) | 134.8, CH | 7.08, d (15.76) |
| 3" | 134.8, CH | 7.04, d (15.76) | 134.2, CH | 6.99, d (15.76) |
| 4" | 168.2, qC | | 168.5, qC | |

Fig. 12

|  | Compound 9 | | Compound 10 | |
| --- | --- | --- | --- | --- |
| position | $\delta_C$, mult. | $\delta_H$ (J in Hz) | $\delta_C$, mult. | $\delta_H$ (J in Hz) |
| 2 | 76.8, qC |  | 75.9, qC |  |
| 2-CH$_3$ | 24.2, CH$_3$ | 1.59, s | 24.2, CH$_3$ | 1.29, s |
| 3 | 31.1, CH$_2$ | 1.73, m | 29.7, CH$_2$ | 1.77, m |
| 4 | 22.3, CH$_2$ | 2.71, m | 22.3, CH$_2$ | 2.74, m |
| 5 | 118.9, CH | 6.55, s | 119.1, CH | 6.70, s |
| 6 | 149.6, qC |  | 149.7, qC |  |
| 7 | 127.1, qC |  | 127.4, qC |  |
| 7-CH$_3$ | 12.1, CH$_3$ | 2.10, s | 12.1, CH$_3$ | 2.14, s |
| 8 | 126.0, qC |  | 126.0, qC |  |
| 8-CH$_3$ | 12.9, CH$_3$ | 2.01, s | 12.9, CH$_3$ | 2.04, s |
| 9 | 118.5, qC |  | 118.6, qC |  |
| 10 | 141.5, qC |  | 141.9, qC |  |
| 1' | 39.8, CH$_2$ | 1.54, 1.63, m | 39.8, CH$_2$ | 1.50, 1.62, m |
| 2' | 22.3, CH$_2$ | 2.07, m | 22.3, CH$_2$ | 2.12, m |
| 3' | 124.5, CH | 5.10, m | 124.5, CH | 5.11, m |
| 4' | 135.3, qC |  | 135.3, qC |  |
| 4'-CH$_3$ | 16.1, CH$_3$ | 1.60, s | 16.1, CH$_3$ | 1.59, s |
| 5' | 39.8, CH$_2$ | 1.97, m | 39.8, CH$_2$ | 1.97, m |
| 6' | 26.8, CH$_2$ | 2.05, m | 26.8, CH$_2$ | 2.04, m |
| 7' | 124.3, CH | 5.10, m | 124.3, CH | 5.11, m |
| 8' | 135.1, qC |  | 135.1, qC |  |
| 8'-CH$_3$ | 16.0, CH$_3$ | 1.60, s | 16.0, CH$_3$ | 1.59, s |
| 9' | 39.8, CH$_2$ | 1.97, m | 39.8, CH$_2$ | 1.97, m |
| 10' | 26.7, CH$_2$ | 2.05, m | 26.7, CH$_2$ | 2.04, m |
| 11' | 124.3, CH | 5.10, m | 124.3, CH | 5.11, m |
| 12' | 131.3, qC |  | 131.3, qC |  |
| 12'a-CH$_3$* | 17.8, CH$_3$ | 1.59, s | 17.8, CH$_3$ | 1.61, s |
| 12'b-CH$_3$* | 25.8, CH$_3$ | 1.67, s | 25.8, CH$_3$ | 1.67, s |
| 1" | 171.5, qC |  | 165.7, qC |  |
| 2" | 40.6, CH$_2$ | 2.60, dd (6.2, 12.8), 2.66, d (5.48) | 129.9, qC |  |
| 3" | 27.4, CH$_2$ | 2.54, m | 130.2, CH | 8.21, dd (1.12, 7.32) |
| 3"-CH$_3$ | 20.0, CH$_3$ | 1.16, d (6.24) |  |  |
| 4" | 40.5, CH$_2$ | 2.37, dd (6.96, 15.4), 2.49, d (6.96) | 128.6, CH | 7.50, dd (7.68, 7.68) |
| 5" | 178.2, qC |  | 133.4, CH | 7.62, brt (7.32) |
| 6" |  |  | 128.6, CH | 7.50, dd (7.68, 7.68) |
| 7" |  |  | 130.2, CH | 8.21, dd (1.12, 7.32) |

Fig. 13

|  | Compound 11 | | Compound 12 | |
| --- | --- | --- | --- | --- |
| position | $\delta_C$, mult. | $\delta_H$ (J in Hz) | $\delta_C$, mult. | $\delta_H$ (J in Hz) |
| 2 | 76.8, qC | | 76.8, qC | --- |
| 2-CH$_3$ | 24.2, CH$_3$ | 1.28, s | 24.2, CH$_3$ | 1.27, s |
| 3 | 31.3, CH$_2$ | 1.78, m | 31.1, CH$_2$ | 1.76, m |
| 4 | 22.3, CH$_2$ | 2.72, m | 22.3, CH$_2$ | 2.73, m |
| 5 | 118.9, CH | 6.64, s | 118.9, CH | 6.64, s |
| 6 | 149.8, qC | | 149.7, qC | |
| 7 | 127.2, qC | | 126.9, C | |
| 7-CH$_3$ | 12.1, CH$_3$ | 2.12, s, 3H | 12.1, CH$_3$ | 2.12, s |
| 8 | 126.1, qC | | 126.6, qC | |
| 8-CH$_3$ | 12.9, CH$_3$ | 2.04, s, 3H | 12.8, CH$_3$ | 2.04, s |
| 9 | 118.6, qC | | 118.5, qC | |
| 10 | 141.6, qC | | 141.6, qC | |
| 1' | 39.8, CH$_2$ | 1.54, 1.62, m | 39.8, CH$_2$ | 1.57, 1.62, m |
| 2' | 22.2, CH$_2$ | 2.10, m | 22.3, CH$_2$ | 2.10, m |
| 3' | 124.5, CH | 5.11, m | 124.5, CH | 5.11, m |
| 4' | 135.3, qC | | 135.3, qC | |
| 4'-CH$_3$ | 16.0, CH$_3$ | 1.59, s | 16.1, CH$_3$ | 1.59, s |
| 5' | 39.8, CH$_2$ | 1.97, m | 39.8, CH$_2$ | 1.96, m |
| 6' | 26.8, CH$_2$ | 2.07, m | 26.8, CH$_2$ | 2.06, m |
| 7' | 124.3, CH | 5.11, m | 124.3, CH | 5.11, m |
| 8' | 135.1, qC | | 135.0, qC | |
| 8'-CH$_3$ | 16.1, CH$_3$ | 1.59, s | 16.0, CH$_3$ | 1.59, s |
| 9' | 39.8, CH$_2$ | 1.97, m | 39.8, CH$_2$ | 1.96, m |
| 10' | 26.7, CH$_2$ | 2.07, m | 26.7, CH$_2$ | 2.06, m |
| 11' | 124.3, CH | 5.11, m | 124.3, CH | 5.11, m |
| 12' | 131.4, qC | | 131.3, qC | |
| 12'a-CH$_3$ | 17.8, CH$_3$ | 1.60, s | 17.8, CH$_3$ | 1.60, s |
| 12'b-CH$_3$ | 25.8, CH$_3$ | 1.67, s | 25.8, CH$_3$ | 1.67, s, |
| 1" | 163.5, qC | | 165.7, qC | |
| 2" | 128.1, qC | | 118.8, CH | 6.59, d (16.12) |
| 3" | 122.8, CH | 7.95, s, 1H of 2H | 144.2, CH | 7.79, d (16.12) |
| 4" | 143.6, qC | | 133.3, qC | |

Fig. 14A

|  | Compound 11 |  | Compound 12 |  |
| --- | --- | --- | --- | --- |
| 4"-OCO(CH$_3$) | 167.8, qC |  |  |  |
| 4"-OCO(CH$_3$) | 20.7, CH$_3$ | 2.31, s |  |  |
| 5" | 139.1, qC |  | 123.0, CH | 7.42, d (1.84) |
| 5"-OCO(CH$_3$) | 166.5, qC |  |  |  |
| 5"-OCO(CH$_3$) | 20.3, CH$_3$ | 2.32, s |  |  |
| 6" | 143.6, qC |  | 143.4, qC |  |
| 6"-OCO(CH$_3$) | 167.8, qC |  | 168.2, qC |  |
| 6"-OCO(CH$_3$) | 20.7, CH$_3$ | 2.31, s | 20.8, CH$_3$ | 2.31, s |
| 7" | 122.8, CH | 7.95, s | 143.8, qC |  |
| 7"-OCO(CH$_3$) |  |  | 168.1, qC |  |
| 7"-OCO(CH$_3$) |  |  | 20.7, CH$_3$ | 2.32, s |
| 8" |  |  | 124.1, CH | 7.25, d (8.08) |
| 9" |  |  | 126.7, CH | 7.46, dd (1.84, 8.4) |

Fig. 14B

TOCOTRIENOL ESTERS

This application claims the benefit of U.S. provisional application 61/301,665 filed Feb. 5, 2010 and entitled "Tocotrienol Esters."

Vitamin E compounds have been shown to exhibit significant activity against cancer cells and in particular mammary epithelial cells with little or no detrimental effect on normal cell growth or function. However, the physicochemical and pharmacokinetic properties of many Vitamin E compounds and Vitamin E based compounds limit the effective use of these compounds in the fight against cancer. Issues such as those relating to chemical stability, water-insolubility, selectivity toward malignant versus normal cells, and rapid metabolism of the compounds have impaired the effective treatment of cancer with these types of compounds. For this reason, compounds and treatment methods with anticancer properties that show potential for improved selectivity, physicochemical, and pharmacokinetic characteristics are needed.

Information relevant to attempts to address these limitations can be found in an article in the British Journal of Cancer by Birringer, M., EyTina, J H., Salvatore, B A., Neuzil, J. Br J Cancer. 2003, 88, 1948-1955 and the book Nutrition and Cancer Prevention by Awad, A. B., Bradford, P. G. (Eds.), CRC Taylor and Francis, Boca Raton 2006, 223-249. However, none of these references has adequately solved the above described needs. For the forgoing reasons, there is a need for compounds and treatment methods with anticancer properties that show potential for improved physicochemical and pharmacokinetic characteristics.

SUMMARY

Disclosed herein are embodiments of the present invention that address the needs described above by providing compounds and methods that are useful in the treatment of cancer and the further development of compounds and methods useful in the treatment of cancer.

Compounds having features of the present invention include for example compounds with the generic structure shown in FIG. 1 and the functional groups indicated in FIG. 3 with reference to FIG. 2 for the higher molecular weight functional groups. These compounds are sometimes referred to herein as Compounds 1-14. Other compounds having features of the present invention include compounds similar to Compounds 1-14 that share the same generic structure from FIG. 1.

A composition of matter having features of the present invention comprises a compound selected from 4-(((R)-2,5,7,8-tetramethyl-2-((3E,7E)-4,8,12-trimethyltrideca-3,7,11-trienyl)chroman-6-yloxy)carbonyl)isophthalic acid; 4-(((R)-2,7,8-trimethyl-2-((3E,7E)-4,8,12-trimethyltrideca-3,7,11-trienyl)chroman-6-yloxy)carbonyl)isophthalic acid; 2-(((R)-2,5,7,8-tetramethyl-2-((3E,7E)-4,8,12-trimethyltrideca-3,7,11-trienyl)chroman-6-yloxy)carbonyl)terephthalic acid; 2-(((R)-2,7,8-trimethyl-2-((3E,7E)-4,8,12-trimethyltrideca-3,7,11-trienyl)chroman-6-yloxy)carbonyl)terephthalic acid; 2-(((R)-2,8-dimethyl-2-((3E,7E)-4,8,12-trimethyltrideca-3,7,11-trienyl)chroman-6-yloxy)-carbonyl)terephthalic acid; (Z)-4-oxo-4-((R)-2,5,7,8-tetramethyl-2-((3E,7E)-4,8,12-trimethyltrideca-3,7,11-trienyl)chroman-6-yloxy)but-2-enoic acid; (Z)-4-oxo-4-((R)-2,7,8-trimethyl-2-((3E,7E)-4,8,12-trimethyltrideca-3,7,11-trienyl)-chroman-6-yloxy)but-2-enoic acid; (Z)-4-((R)-2,8-dimethyl-2-((3E,7E)-4,8,12-trimethyltrideca-3,7,11-trienyl)chroman-6-yloxy)-4-oxobut-2-enoic acid; 3-Methyl-5-oxo-5-((R)-2,7,8-trimethyl-2-((3E,7E)-4,8,12-trimethyltrideca-3,7,11-trienyl)chroman-6-yloxy)pentanoic acid; (R)-2,7,8-trimethyl-2-((3E,7E)-4,8,12-trimethyltrideca-3,7,11-trienyl)chroman-6-yl benzoate; 5-(((R)-2,7,8-trimethyl-2-((3E,7E)-4,8,12-trimethyltrideca-3,7,11-trienyl)chroman-6-yloxy)carbonyl)benzene-1,2,3-triyl triacetate; 4-((E)-3-oxo-3-((R)-2,7,8-trimethyl-2-((3E,7E)-4,8,12-trimethyltrideca-3,7,11-trienyl)chroman-6-yloxy)prop-1-enyl)-1,2-phenylene diacetate; (R)-2,7,8-trimethyl-2-((3E,7E)-4,8,12-trimethyltrideca-3,7,11-trienyl)chroman-6-yl 3,4,5-trihydroxybenzoate; and (E)-((R)-2,7,8-trimethyl-2-((3E,7E)-4,8,12-trimethyltrideca-3,7,11-trienyl)chroman-6-yl) 3-(3,4-dihydroxyphenyl)acrylate. Each of the individual aforementioned compounds represent a composition of matter having features of the present invention.

The composition of matter having features of the present invention comprises: one or more compounds having a farnesyl side chain; a first compound selected from one or more compounds having a farnesyl side chain; wherein the first compound is a compound having the predominant potency among the one or more compound having a farnesyl side chain; wherein the first compound is selected from: 4-(((R)-2,5,7,8-tetramethyl-2-((3E,7E)-4,8,12-trimethyltrideca-3,7,11-trienyl)chroman-6-yloxy)carbonyl)isophthalic acid; 4-(((R)-2,7,8-trimethyl-2-((3E,7E)-4,8,12-trimethyltrideca-3,7,11-trienyl)chroman-6-yloxy)carbonyl)isophthalic acid; 2-(((R)-2,5,7,8-tetramethyl-2-((3E,7E)-4,8,12-trimethyltrideca-3,7,11-trienyl)chroman-6-yloxy)carbonyl)terephthalic acid; 2-(((R)-2,7,8-trimethyl-2-((3E,7E)-4,8,12-trimethyltrideca-3,7,11-trienyl)chroman-6-yloxy)carbonyl) terephthalic acid; 2-(((R)-2,8-dimethyl-2-((3E,7E)-4,8,12-trimethyltrideca-3,7,11-trienyl)chroman-6-yloxy)-carbonyl) terephthalic acid; (Z)-4-oxo-4-(R)-2,5,7,8-tetramethyl-2-((3E,7E)-4,8,12-trimethyltrideca-3,7,11-trienyl)chroman-6-yloxy)but-2-enoic acid; (Z)-4-oxo-4-((R)-2,7,8-trimethyl-2-((3E,7E)-4,8,12-trimethyltrideca-3,7,11-trienyl)-chroman-6-yloxy)but-2-enoic acid; (Z)-4-((R)-2,8-dimethyl-2-((3E,7E)-4,8,12-trimethyltrideca-3,7,11-trienyl)chroman-6-yloxy)-4-oxobut-2-enoic acid; 3-Methyl-5-oxo-5-((R)-2,7,8-trimethyl-2-((3E,7E)-4,8,12-trimethyltrideca-3,7,11-trienyl)chroman-6-yloxy)pentanoic acid; (R)-2,7,8-trimethyl-2-((3E,7E)-4,8,12-trimethyltrideca-3,7,11-trienyl)chroman-6-yl benzoate; 5-(((R)-2,7,8-trimethyl-2-((3E,7E)-4,8,12-trimethyltrideca-3,7,11-trienyl)chroman-6-yloxy)carbonyl)benzene-1,2,3-triyl triacetate; 4-((E)-3-oxo-3-((R)-2,7,8-trimethyl-2-((3E,7E)-4,8,12-trimethyltrideca-3,7,11-trienyl)chroman-6-yloxy)prop-1-enyl)-1,2-phenylene diacetate; (R)-2,7,8-trimethyl-2-((3E,7E)-4,8,12-trimethyltrideca-3,7,11-trienyl)chroman-6-yl 3,4,5-trihydroxybenzoate; and (E)-((R)-2,7,8-trimethyl-2-((3E,7E)-4,8,12-trimethyltrideca-3,7,11-trienyl)chroman-6-yl) 3-(3,4-dihydroxyphenyl) acrylate.

A composition of matter having features of the present invention comprises a compound that is an both an ester and a carboxylic acid; wherein the compound has both a farnesyl side chain and a chroman ring; wherein the compound contains a functional group selected from a hydrogen bond donating group and a hydrogen bond accepting group; wherein the functional group is separated by no more than four carbon atoms from an oxygen that is bonded to the chroman ring; and wherein the functional group is not a part of the farnesyl side chain or the chroman ring. A composition of matter containing Compound 6 would be an example of such a composition.

Embodiments of the invention also include methods of treating and preventing forms of cancer by administering a compound of the type taught herein to mammalian patients. Further embodiments of the invention include exposing mammalian cells to therapeutic amounts of compounds disclosed herein. Still further embodiments of the invention include compositions that are the product of administering compounds of the present invention to a mammalian patient. Still other embodiments of the invention include compositions that are the product of the reaction of an acyl chloride with a tocotrienol.

BRIEF DESCRIPTION OF THE DRAWING

FIG. 3 of the drawings is a table indicating how each functional group is configured to form Compounds 1-14 based on the structure of FIG. 1 and functional groups "a"-"g" of FIG. 2.

FIG. 9 shows $^1$H and $^{13}$C NMR Data for Compounds 1 and 2.

FIG. 10 shows $^1$H and $^{13}$C NMR Data for Compounds 3 and 4.

FIG. 11 shows $^1$H and $^{13}$C NMR Data for Compounds 5 and 6.

FIG. 12 shows $^1$H and $^{13}$C NMR Data for Compounds 7 and 8.

FIG. 13 shows $^1$H and $^{13}$C NMR Data for Compounds 9 and 10.

FIG. 14A shows $^1$H and $^{13}$C NMR Data for Compounds 11 and 12 with data continuing to FIG. 14B.

DETAILED DESCRIPTION

Figure 1:
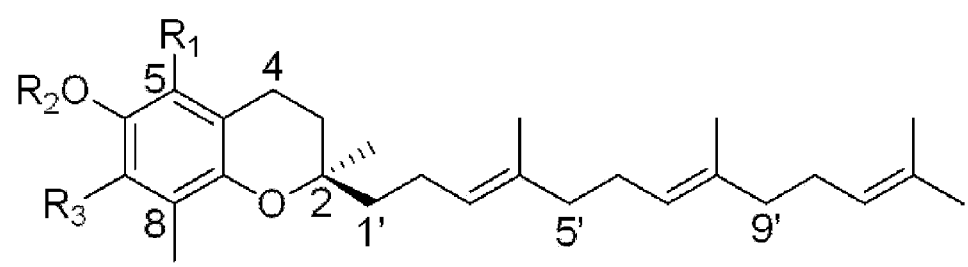
FIG. 1 of the drawings is a chemical structure drawing of the basic structure of certain compounds of the invention.

The Compounds 1-12 were synthesized from tocotrienols as described below. The compounds were then tested for various activities pertinent to the treatment of cancer. The following descriptions detail the characteristics of those compounds, their preparation and their use.

Compounds 4-(((R)-2,5,7,8-tetramethyl-2-((3E,7E)-4,8,12-trimethyl-tridec-3,7,11-trienyl)chroman-6-yloxy)carbonyl)isophthalic acid, sometimes referred to herein as Compound 1, is a yellow viscous oil with the following characteristics: UV $\lambda_{max}$ (nm) 288; $[\alpha]_D^{25}$ +2.5 (c 0.16, CHCl$_3$); IR (neat) $\upsilon_{max}$: 3626, 2926.4, 1740, 1706.9, 1230.3, cm$^{-1}$; $^1$H and $^{13}$C NMR: see FIG. 9; HREIMS: (M−H)$^+$ m/z 615.3323 (Calcd for C$_{38}$H$_{48}$O$_7$: 616.3400). Compound 1 may be represented by the general formula of FIG. 1 wherein R$_1$ is CH$_3$, R$_2$ is functional group "a" from FIG. 2, and R$_3$ is CH$_3$.

4-(((R)-2,7,8-trimethyl-2-((3E,7E)-4,8,12-trimethyl-tridec-3,7,11-trienyl)chroman-6-yloxy)carbonyl)isophthalic acid, sometimes referred to herein as Compound 2, is a yellowish white semisolid with the following characteristics: UV $\lambda_{max}$ (nm) 286; $[\alpha]_D^{25}$ 0.0 (c 0.08, CHCl$_3$); IR (neat) $\upsilon_{max}$: 3623, 2832.9, 2305.4, 1720.5, 1263.3 cm$^{-1}$; $^1$H and $^{13}$C NMR: see FIG. 9; HREIMS: (M−H)$^+$ m/z 601.3165 (Calcd for C$_{37}$H$_{46}$O$_7$: 602.3244). Compound 2 may be represented by the general formula of FIG. 1 wherein R$_1$ is H, R$_2$ is functional group "a" from FIG. 2, and R$_3$ is CH$_3$.

2-(((R)-2,5,7,8-tetramethyl-2-((3E,7E)-4,8,12-trimethyl-tridec-3,7,11-trienyl)chroman-6-yloxy)carbonyl)terephthalic acid, sometimes referred to herein as Compound 3, is a yellowish white semisolid with the following characteristics: UV $\lambda_{max}$ (nm) 284; $[\alpha]_D^{25}$ −2.3 (c 0.04, CHCl$_3$); IR (neat) $\upsilon_{max}$: 3625, 3054, 2986, 2305, 1738, 1605, 1422, 1018 cm$^{-1}$; $^1$H and $^{13}$C NMR: see FIG. 10; HREIMS: (M−H)$^+$ m/z 615.3328 (Calcd for C$_{38}$H$_{48}$O$_7$: 616.3400). Compound 3 may be represented by the general formula of FIG. 1 wherein R$_1$ is CH$_3$, R$_2$ is functional group "b" from FIG. 2, and R$_3$ is CH$_3$.

2-(((R)-2,7,8-trimethyl-2-((3E,7E)-4,8,12-trimethyl-tridec-3,7,11-trienyl)chroman-6-yloxy)carbonyl)terephthalic acid, sometimes referred to herein as Compound 4, is a yellowish white semisolid with the following characteristics: UV $\lambda_{max}$ (nm) 290, 274; $[\alpha]_D^{25}$ 0.0 (c 0.19, CHCl$_3$); IR (neat) $\upsilon_{max}$: 2927, 1742, 1705, 1228, 1102 cm$^{-1}$; $^1$H and $^{13}$C NMR: see FIG. 10; HREIMS: (M−H)$^+$ m/z 601.3170 (Calcd for C$_{37}$H$_{46}$O$_7$: 602.3244). Compound 4 may be represented by the general formula of FIG. 1 wherein R$_1$ is H, R$_2$ is functional group "b" from FIG. 2, and R$_3$ is CH$_3$.

2-(((R)-2,8-dimethyl-2-((3E,7E)-4,8,12-trimethyl-tridec-3,7,11-trienyl)chroman-6-yloxy)-carbonyl)terephthalic acid, sometimes referred to herein as Compound 5, is a yellowish white semisolid with the following characteristics: UV $\lambda_{max}$ (nm) 290; $[\alpha]_D^{25}$ −2.5 (c 0.04, CHCl$_3$); IR (neat) $\upsilon_{max}$: 3054, 2986, 2305, 1741, 1705, 1422, 1154 cm$^{-1}$; $^1$H and $^{13}$C NMR: see FIG. 11; HREIMS: (M−H)$^+$ m/z 587.3014 (Calcd for C$_{36}$H$_{44}$O$_6$: 588.3087). Compound 5 may be represented by the general formula of FIG. 1 wherein R$_1$ is H, R$_2$ is functional group "b" from FIG. 2, and R$_3$ is H.

(Z)-4-oxo-4-((R)-2,5,7,8-tetramethyl-2-((3E,7E)-4,8,12-trimethyltridec-3,7,11-trienyl)chroman-6-yloxy)but-2-enoic acid, sometimes referred to herein as Compound 6, is a yellow viscous oil with the following characteristics: UV $\lambda_{max}$ (nm) 284, 276; $[\alpha]_D^{25}$ −48.8 (c 0.08, CHCl$_3$); IR (neat) $\upsilon_{max}$: 3054, 2933, 2857, 2305, 1736, 1710, 1230, 1152 cm$^{-1}$; $^1$H and $^{13}$C NMR: see FIG. 11; HREIMS: (M−H)$^+$ m/z 521.3269 (Calcd for C$_{33}$H$_{46}$O$_5$: 522.3345). Compound 6 may be represented by the general formula of FIG. 1 wherein R$_1$ is CH$_3$, R$_2$ is functional group "c" from FIG. 2, and R$_3$ is CH$_3$.

(Z)-4-oxo-4-((R)-2,7,8-trimethyl-2-((3E,7E)-4,8,12-trimethyltrideca-3,7,11-trienyl)-chroman-6-yloxy)but-2-enoic acid, sometimes referred to herein as Compound 7, is a yellow viscous oil with the following characteristics: UV $\lambda_{max}$ (nm) 288; $[\alpha]_D^{25}$ −36.6 (c 0.03, CHCl$_3$); IR (neat) $\upsilon_{max}$: 3054, 2987, 2685, 2360, 2306, 1734, 1605, 1421, 1157 cm$^{-1}$; $^1$H and $^{13}$C NMR: see FIG. 12; HREIMS: (M–H)$^+$ m/z 507.3118 (Calcd for $C_{32}H_{44}O_5$: 508.3189). Compound 7 may be represented by the general formula of FIG. 1 wherein $R_1$ is H, $R_2$ is functional group "c" from FIG. 2, and $R_3$ is $CH_3$.

(Z)-4-((R)-2,8-dimethyl-2-((3E,7E)-4,8,12-trimethyl-trideca-3,7,11-trienyl)chroman-6-yloxy)-4-oxobut-2-enoic acid, sometimes referred to herein as Compound 8, is a yellow viscous oil with the following characteristics: UV $\lambda_{max}$ (nm) 288, 278; $[\alpha]_D^{25}$ 12.8 (c 0.023, CHCl$_3$); IR (neat) $\upsilon_{max}$: 3054, 2987, 2685, 2360, 2306, 1734, 1605, 1421, 11266 cm$^{-1}$; $^1$H and $^{13}$C NMR: see FIG. 12; HREIMS: (M–H)$^+$ m/z 493.2960 (Calcd for $C_{31}H_{42}O_5$: 494.3032). Compound 8 may be represented by the general formula of FIG. 1 wherein $R_1$ is H, $R_2$ is functional group "c" from FIG. 2, and $R_3$ is H.

3-Methyl-5-oxo-5-((R)-2,7,8-trimethyl-2-((3E,7E)-4,8,12-trimethyltrideca-3,7,11-trienyl)chroman-6-yloxy)pentanoic acid, sometimes referred to herein as Compound 9, is a white yellowish viscous oil with the following characteristics: UV $\lambda_{max}$ (nm) 288, 282; $[\alpha]_D^{25}$ –2.3 (c 0.39, CHCl$_3$); IR (neat) $\upsilon_{max}$: 3626, 2927, 2856, 1711, 1476, 1377, 1198 cm$^{-1}$; $^1$H and $^{13}$C NMR: see FIG. 13; HREIMS: (M–H)$^+$ m/z 537.3585 (Calcd for $C_{34}H_{50}O_5$: 538.3658). Compound 9 may be represented by the general formula of FIG. 1 wherein $R_1$ is H, $R_2$ is functional group "d" from FIG. 2, and $R_3$ is $CH_3$.

(R)-2,7,8-trimethyl-2-((3E,7E)-4,8,12-trimethyltrideca-3,7,11-trienyl)chroman-6-yl benzoate, sometimes referred to herein as Compound 10, is a white yellowish viscous oil with the following characteristics: UV $\lambda_{max}$ (nm) 282; $[\alpha]_D^{25}$ –4.6 (c 0.065, CHCl$_3$); IR (neat) $\upsilon_{max}$: 2927, 2855, 1731, 1602, 1229, 1094 cm$^{-1}$; $^1$H and $^{13}$C NMR: see FIG. 13; HREIMS: (M–H)$^+$ m/z 437.3421 (Calcd for $C_{36}H_{48}O_2$: 512.3654). Compound 10 may be represented by the general formula of FIG. 1 wherein $R_1$ is H, $R_2$ is functional group "e" from FIG. 2, and $R_3$ is $CH_3$.

5-(((R)-2,7,8-trimethyl-2-((3E,7E)-4,8,12-trimethyl-trideca-3,7,11-trienyl)chroman-6-yloxy)carbonyl)benzene-1,2,3-triyl triacetate, sometimes referred to herein as Compound 11, is a yellowish white semisolid with the following characteristics: UV $\lambda_{max}$ (nm) 286; $[\alpha]_D^{25}$ –6.0 (c 0.13, CHCl$_3$); IR (neat) $\upsilon_{max}$: 2928, 2856, 2303, 1782, 1736, 1612, 1493, 1371, 1326, 1190 cm$^{-1}$; $^1$H and $^{13}$C NMR: see FIGS. 14A and 14B; HREIMS: (M+H)$^+$ m/z 689.3690 (Calcd for $C_{41}H_{52}O_9$: 688.3611). Compound 11 may be represented by the general formula of FIG. 1 wherein $R_1$ is H, $R_2$ is functional group "f" from FIG. 2, and $R_3$ is $CH_3$.

4-((E)-3-oxo-3-((R)-2,7,8-trimethyl-2-((3E,7E)-4,8,12-trimethyltrideca-3,7,11-trienyl)chroman-6-yloxy)prop-1-enyl)-1,2-phenylene diacetate, sometimes referred to herein as Compound 12, is a yellow oil with the following characteristics: UV $\lambda_{max}$ (nm) 284, 278; $[\alpha]_D^{25}$ 10 (c 0.03, CHCl$_3$); IR (neat) $\upsilon_{max}$: 3054, 2927, 2855, 1774, 1725, 1641, 1205 cm$^{-1}$; $^1$H and $^{13}$C NMR: see FIGS. 14A and 14B; HREIMS: (M+H)$^+$ m/z 657.3772 (Calcd for $C_{41}H_{52}O_7$: 656.3713). Compound 12 may be represented by the general formula of FIG. 1 wherein $R_1$ is H, $R_2$ is functional group "g" from FIG. 2, and $R_3$ is $CH_3$.

(R)-2,7,8-trimethyl-2-((3E,7E)-4,8,12-trimethyltrideca-3,7,11-trienyl)chroman-6-yl-3,4,5-trihydroxybenzoate, is sometimes referred to herein as Compound 13. Compound 13 may be represented by the general formula of FIG. 1 wherein $R_1$ is H, $R_2$ is functional group "h" from FIG. 2, and $R_3$ is $CH_3$.

(E)-((R)-2,7,8-trimethyl-2-((3E,7E)-4,8,12-trimethyl-trideca-3,7,11-trienyl)chroman-6-yl) 3-(3,4-dihydroxyphenyl)acrylate, is sometimes referred to herein as Compound 14. Compound 14 may be represented by the general formula of FIG. 1 wherein $R_1$ is H, $R_2$ is functional group "i" from FIG. 2, and $R_3$ is $CH_3$.

Compounds 1-14 may also be described by reference to FIG. 3 which indicates the arrangement of functional groups, including those shown in FIG. 2, on the generalized structure shown in FIG. 1 for each of Compounds 1-14.

Figure 2:
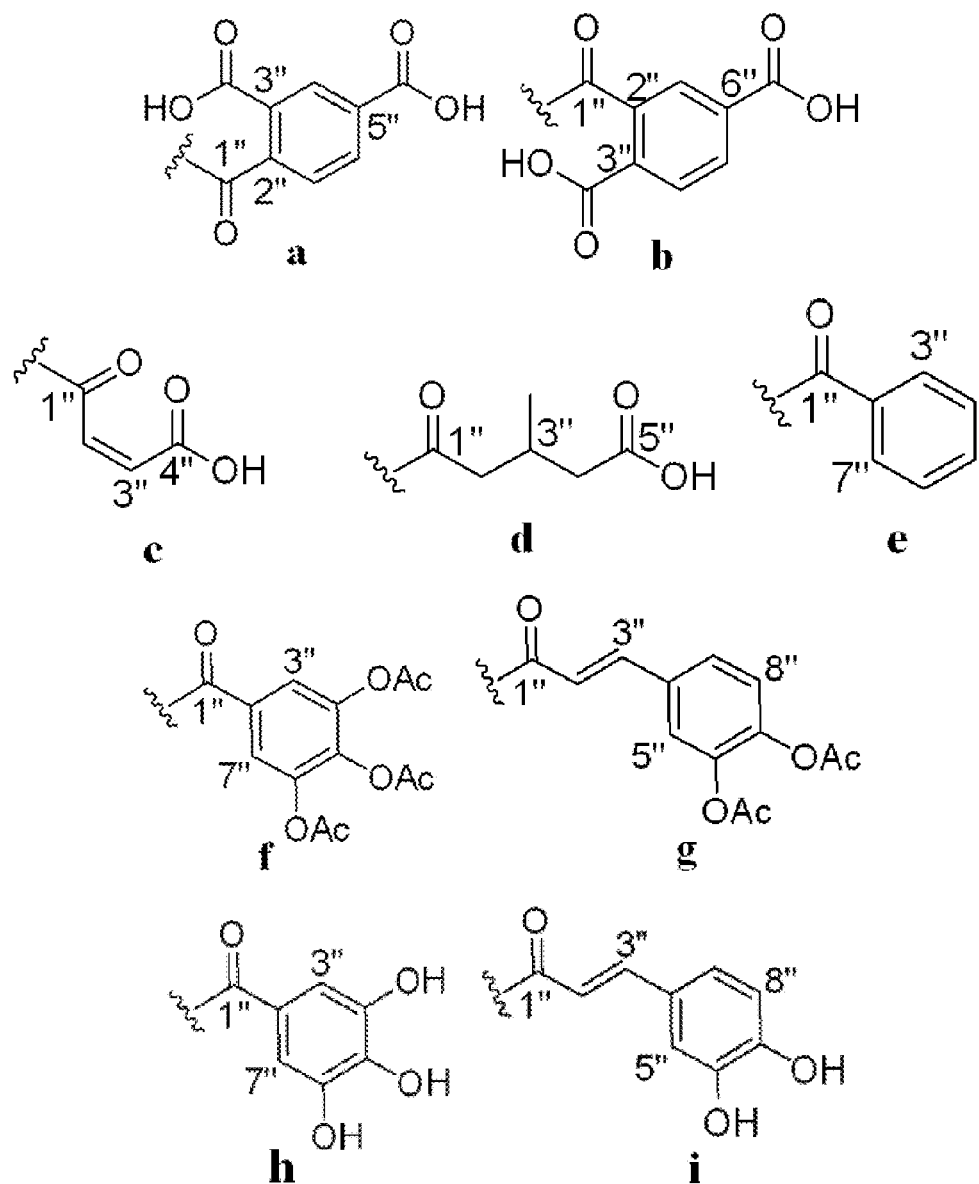
FIG. 2 of the drawings is a collection of functional groups that join with the basic structure of FIG. 1 at the position $R_2$.

Referring to FIGS. 1 and 2 of the drawings multiple embodiments of the invention may take the form of the chemical structure of FIG. 1 wherein $R_1$ is either H or $CH_3$, $R_3$ is either H or $CH_3$; and wherein $R_2$ is one of the functional groups presented in FIG. 2. In one of those embodiments $R_2$ is functional group "a" and $R_3$ is $CH_3$. In another such embodiment, $R_1$ is $CH_3$ and $R_2$ is functional group "b." In still another such embodiment $R_1$ is H and $R_2$ is functional group "b." In still another such embodiment, $R_2$ is functional group "b" and $R_3$ is $CH_3$. In still another such embodiment, $R_2$ is functional group "b" and $R_3$ is H. In still another such embodiment, $R_1$ is $CH_3$ and $R_2$ is functional group "c." In still another such embodiment, $R_1$ is H and $R_2$ is functional group "c." In still another such embodiment, $R_2$ is functional group "c" and $R_3$ is $CH_3$. In still another such embodiment $R_2$ is functional group "c" and $R_3$ is H. In still another such embodiment, $R_1$ is H and $R_3$ is $CH_3$. In separate embodiments of the invention wherein $R_1$ is H and $R_3$ is $CH_3$, $R_2$ is one of functional groups "d," "e," "f," "g," "h," and "i." In still another embodiment, the functional group $R_2$ contains an aromatic ring.

Compound Preparation

Compounds 1-10 were prepared from the acid anhydrides indicated in Table 1 below.

TABLE 1

| Compound(s) | Starting acid anhydride |
| --- | --- |
| 1 & 2 | 1,2,4-Benzenetricarboxylic anhydride |
| 3, 4, & 5 | 1,2,4-Benzenetricarboxylic anhydride |
| 6, 7, & 8 | Maleic anhydride |
| 9 | 3-Methylglutaric acid anhydride |
| 10 | Benzoic acid anhydride |

5.7 mmol of acid anhydride and 5.7 mmol of dicyclohexylcarbodiimide were added to a dry pyridine solution of tocotrienol (4.8 mmol). The reaction mixture was stirred at room temperature for 20 hours and the dicyclohexylurea formed was removed by filtration. After the solvent was evaporated, the residue was treated with 100 ml of water and made alkaline by sodium bicarbonate. The solution was then extracted with ethyl acetate (100 ml 3 times). The organic layer was dried over anhydrous magnesium sulfate and evaporated. The residue was purified by column chromatography either by silica gel 60 (particle size 0.063-0.2 mm, 70-230 mesh ASTM) packed column using ethylacetate:methanol (92.5: 7.5) as mobile system, or by silica-RP18 using methanol: water gradient elution yielding Compounds 1-10.

Figure 7A:
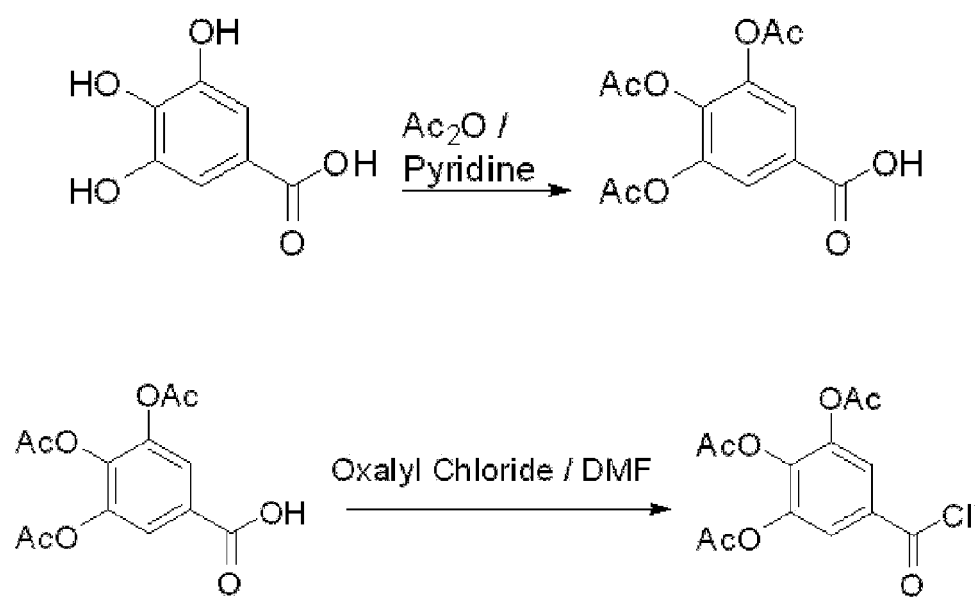
FIG. 7A shows reactions that are part of the preparation of the acyl chloride intermediate of Compound 11.
Figure 7B:
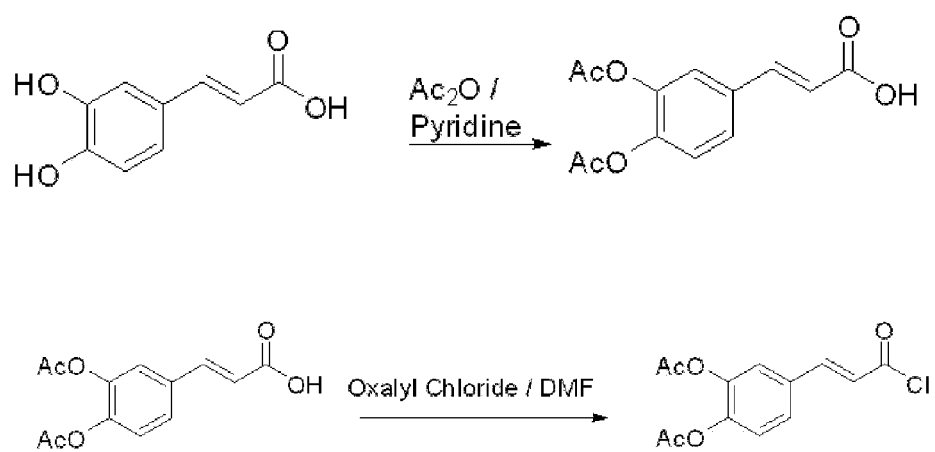
FIG. 7B shows reactions that are part of the preparation of the acyl chloride intermediate of Compound 12.

Compounds 11 and 12 are prepared by the esterification of tocotrienols using acyl chlorides in a manner similar to that described in the article Synthesis of Selenium-Containing Polyphenolic Acid Esters and Evaluation of Their Effects on Antioxidation and 5-Lipoxygenase Inhibition by Lin, C-F., Chang, T-C., Chiang, C-C., Tsai, H-I., Hsu, L-Y. Chem. Pharm. Bull. 2005, 53, 1402-1407. Preparation of Compounds 11 and 12 carried out by preparing 3,4,5-triacetylbenzoyl chloride and 3,4-diacetylcinnamoyl chloride from gallic and caffeic acid respectively. The steps of these two reaction sequences are illustrated in FIGS. 7A and 7B respectively. The acyl chlorides were prepared by adding acetic anhydride (6 eq) and pyridine (2 ml) to a solution of either gallic or caffeic acid (20 mmol). The mixture was stirred at room temperature in the dark for 4 hours and then poured onto 1M $H_3PO_4$ (10 ml) cold solution. The mixture was extracted with ethyl acetate. The layers were washed with brine and aqueous saturated sodium bicarbonate. The combined organic phase was dried under magnesium sulfate, filtered, and the solvent was removed under a vacuum to afford the corresponding acetoxy polyphenolic acids: 3,4,5-triacetoxy benzoic acid, and 3,4-diacetoxy cinnamic acid. These acetoxy polyphenolic acids were identified by NMR. Data were in agreement with literature values. Oxalyl chloride (0.7 ml) was added to a solution of the acetoxy polyphenolic acid (5 mmol) and dry dichloromethane (10 ml) and the mixture was stirred for 8 hours at room temperature. The mixture is concentrated under vacuum to give either 3,4,5-triacetylbenzoyl chloride or 3,4-diacetylcinnamoyl chloride to be used for the esterification of tocotrienol.

Dry dichloromethane (10 ml), triethylamine (5 ml), and tocotrienol (1.2 eq) were added at 0° C. to a concentrated mixture of either 3,4,5-triacetylbenzoyl chloride or 3,4-diacetylcinnamoyl chloride. The reaction mixture was stirred over night and then poured onto ice water. The mixture was extracted three times with ethyl acetate. The combined organic phase was dried under magnesium sulfate, filtered, and the solvent was removed in a vacuum. The residue was purified on silica gel 60 (particle size 0.063-0.2 mm, 70-230 mesh ASTM) packed column using n-hexane/ethyl acetate as mobile system.

Figure 8:
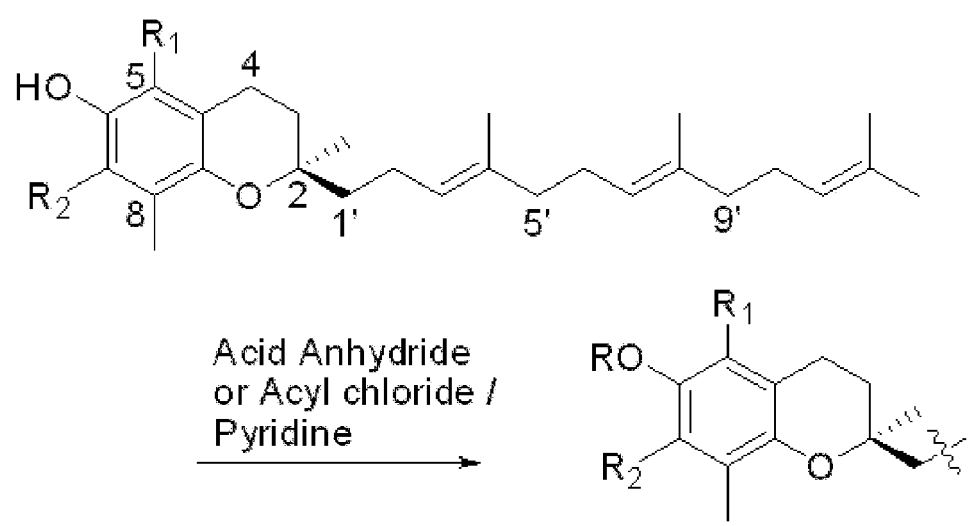
FIG. 8 shows a generalized version of the final reaction step in the preparation of Compounds 1-12.

FIG. 8 is an illustration of the generalized reaction that is the final reaction step for the preparation of each of Compounds 1-12.

Several compositions of matter having features of the present invention may be characterized as compositions of matter that are the tocotrienol based reaction product of an acylating acid with a tocotrienol wherein the acylating acid has a pKa of about 3 or less and the acylating acid has at least one carbon-carbon double bond. In a related embodiment, the acylating acid has a pKa of about 2 or less. In a further related embodiment, the acylating acid has at least one terminal free ionizable group also present in the tocotrienol based product. In a still further related embodiment, the tocotrienol based product is present in a therapeutic amount. In a still further related embodiment, neither of the carbons of the at least one carbon-carbon double bond is a member of an aromatic ring. In a still further related embodiment, the composition of matter is capable of demonstrating an activity greater than that of the tocotrienol from which it was derived when administered to a human patient in vivo at a comparable dosage rate on a molar basis. In two additional separate but related embodiments, the molecular weight of the tocotrienol based product is at least about 507 and at least about 450. In still two further separate but related embodiments, the molecular weight of the tocotrienol based product is at most about 698 and at most about 800. In a still further related embodiment, the tocotrienol based product has greater water solubility than the tocotrienol. In a still further related embodiment, the tocotrienol based product has a water solubility of about that of (R)-2,7,8-trimethyl-2-((3E,7E)-4,8,12-trimethyltrideca-3,7,11-trienyl)chroman-6-yl benzoate or greater. In a still further related embodiment, the acylating acid has a log P value of about 1.0 or less. In a still further related embodiment, the acylating acid has a log P value of about 0.7 or less. In a still further related embodiment, the tocotrienol based product has greater polarity than the tocotrienol. In a still further related embodiment, the tocotrienol based product has a polarity of about that of (R)-2,7,8-trimethyl-2-((3E,7E)-4,8,12-trimethyltrideca-3,7,11-trienyl)chroman-6-yl benzoate or greater.

In a prophetic example, Compounds 13 and 14 are prepared by the oral administration of Compounds 11 and 12 respectively to a mammal. It is believed that during the natural process of digestion and absorption of Compounds 11 and 12 enzymes convert Compounds 11 and 12 to Compounds 13 and 14 respectively. Similar preparation could be done outside of the body based on the selection of an appropriate enzyme.

Antiproliferative Assays

+SA mammary epithelial cell lines were serially passaged at subconfluent cell density. The +SA cell line was derived from an adenocarcinoma that developed spontaneously in a BALB/c female mouse. That cell line is discussed in more detail in Anderson, L. W., Danielson, K. G., Hosick, H. L. *Eur. J. Cancer Clin. Oncol.* 1981, 17, 1001-1008, Danielson, K G., Anderson, L. W., Hosick, H. L. *Cancer Res.* 1980, 40, 1812-1819.31, and Anderson, L. W., Danielson, K. G., Hosick, H. L. *In Vitro.* 1979, 15, 841-843. Cell culture conditions were similar to those described in detail in Shah, S. J., Gapor, A., Sylvester, P. W. Nutr. Cancer. 2003, 45, 236-246, Shah, S. J., Sylvester, P. W. Biochem. Cell. Biol. 2005, 83, 86-95, Wali, V. B., Sylvester, P. W. *Lipids,* 2007, 42, 1113-1123, and Wali, V. B., Bachawal, S. V., Sylvester, P. W. *Exp. Biol. Med.* (Maywood) 2009, 234, 639-650. Briefly, +SA cells were maintained in serum-free defined medium consisting of Dulbecco's modified Eagle's medium (DMEM)/F12 containing 5 mg/ml bovine serum albumin (BSA), 10 mg/ml transferrin, 100 U/ml soybean trypsin inhibitor, 100 U/ml penicillin, 0.1 mg/ml streptomycin, 10 mg/ml insulin, and 10 ng/ml epidermal growth factor. For subculturing, cells were rinsed twice with sterile $Ca^{2+}$ and $Mg^{2+}$-free phosphate buffered saline (PBS) and incubated in 0.05% trypsin containing 0.025% EDTA in PBS for 5 minutes at 37° C. The released cells were centrifuged, resuspended in serum-free defined media and counted using a hemocytometer. A stock solution of the Compounds was prepared in DMSO. Once dissolved, this solution was added to a small volume of sterile 10% BSA in water and incubated overnight at 37° C. This solution conjugated to BSA was used to prepare various concentrations (0-40 µM) of tocotrienol analogs. DMSO was added to all treatment media such that the final DMSO concentration was the same in all treatment groups within a given experiment and was always less than 0.1%. For cytotoxicity studies, cells were seeded at a density of $5 \times 10^4$ cells/well (6 wells/group) in 24-well culture plates and allowed to grow in serum-free control defined media. After a 3 day incubation period (approximately 70% confluency), cells were divided equally into various treatment groups and exposed to their respective treatments for a 24 hour incubation period. Following the 24 hour treatment period, cell viability was measured using the MTT assay. All materials were purchased from Sigma Chemical Company (St. Louis, Mo.) unless otherwise stated.

Figure 4:
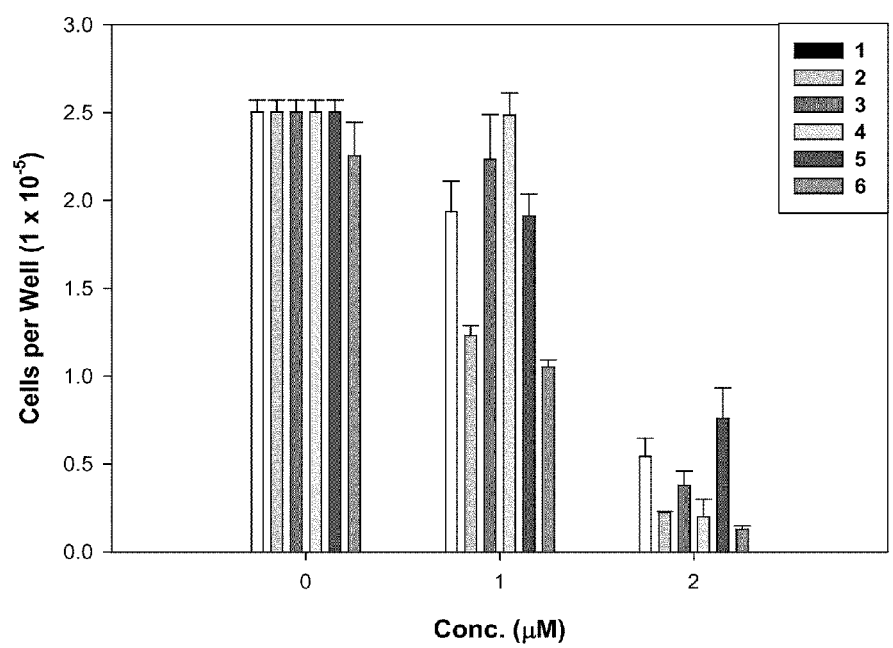
FIG. 4 shows the impact of Compounds 1-6 on +SA mammary tumor cell viability at various concentrations.
Figure 5:
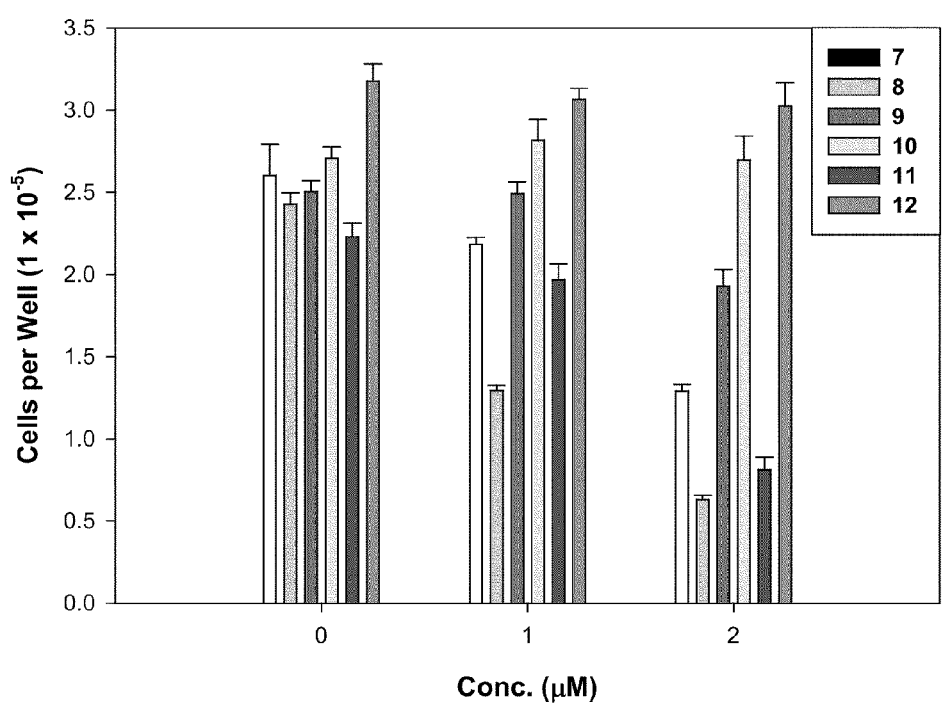
FIG. 5 shows the impact of Compounds 7-12 on +SA mammary tumor cell viability at various concentrations.

+SA mammary epithelial cell viable number was determined by the 3-(4,5-dimethylthiazol-2-yl)-2,5-diphenyl tetrazolium bromide (MTT) colorimetric assay. On the day of assay, treatment medium was replaced with fresh growth medium containing 0.42 mg/ml MTT, and the cells in 24-well plates were incubated at 37° C. for 4 hours. Afterward, the medium was removed, and the MTT crystals were dissolved in isopropyl alcohol (1 ml/well). The optical density of each sample was read at 570 nm on a microplate reader (SpectraCount, Packard BioScience Company), against a blank prepared from cell-free cultures. The number of cells/well was calculated against a standard curve prepared by plating various concentrations of cells, as determined by hemocytometer, at the start of each experiment. FIG. 4 shows the effects of treatment exposures of Compounds 1-6 on the viability of +SA mammary tumor cells at various μM concentrations. FIG. 5 shows the effects of treatment exposures of Compounds 7-12 on the viability of +SA mammary tumor cells at various μM concentrations.

Figure 17:
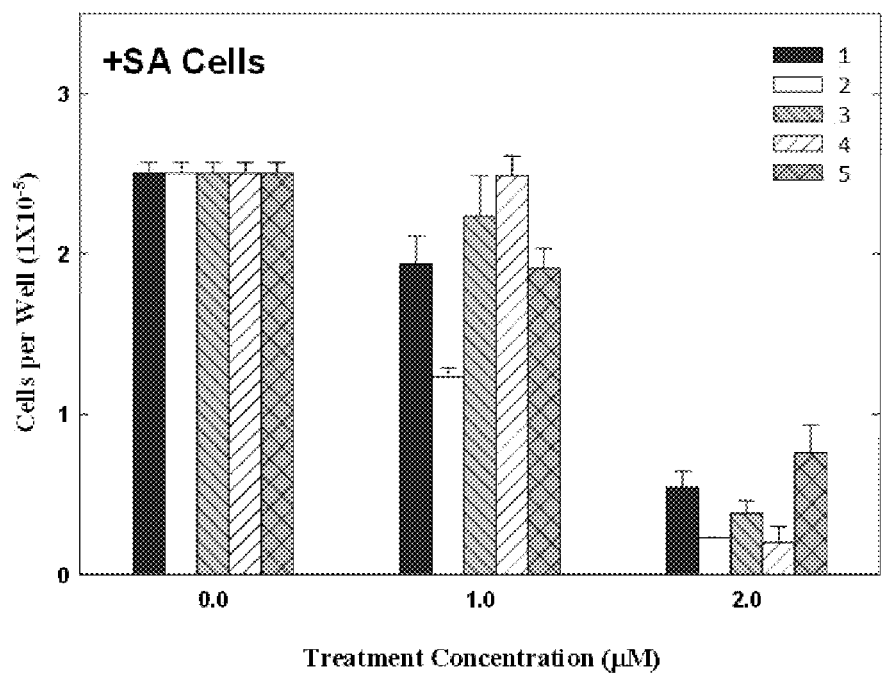
FIG. 17 is a graph of the effects of various treatments of tocotrienol analogues, Compounds 1-5, on the viability of the neoplastic +SA mammary cells.
Figure 18:
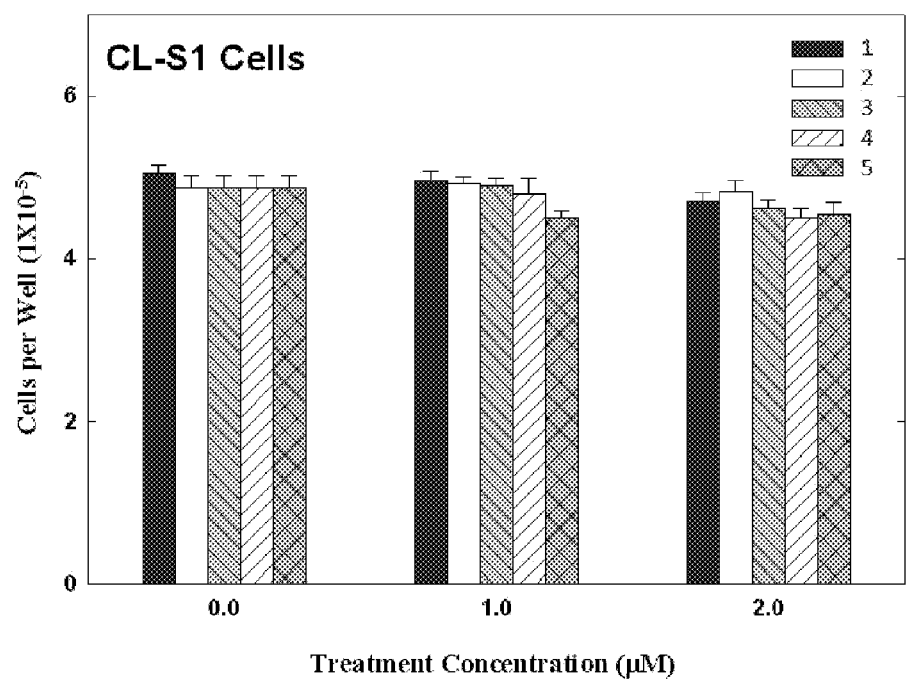
FIG. 18 is a graph of the effects of various treatments of tocotrienol analogues, Compounds 1-5, on the viability of the normal mammary cells CL-S1.
Figure 19:
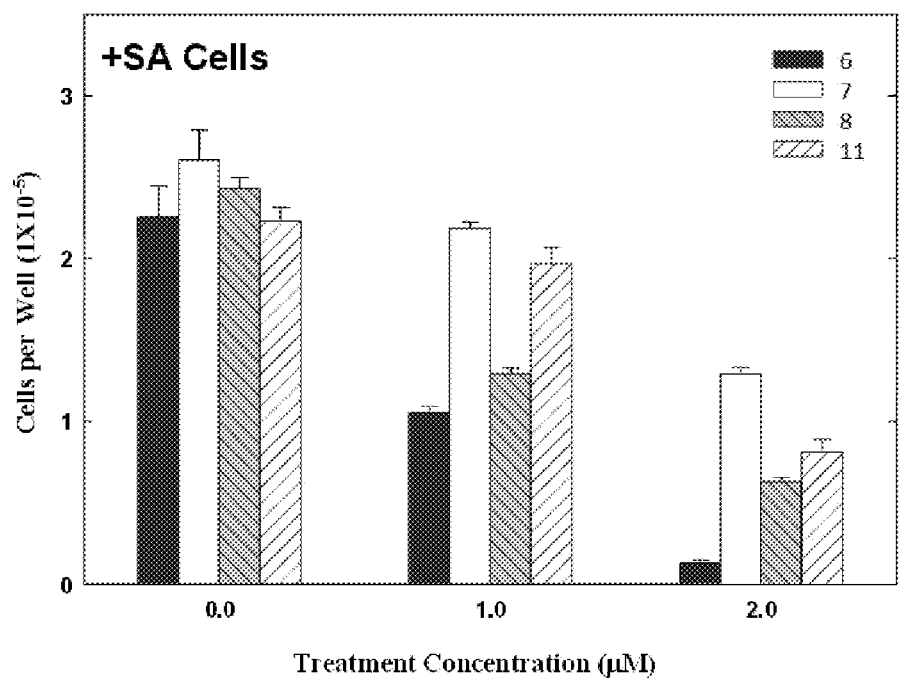
FIG. 19 is a graph of the effects of various treatments of tocotrienol analogues, Compounds 6-8 and 11 on the viability of the neoplastic +SA mammary cells.
Figure 20:
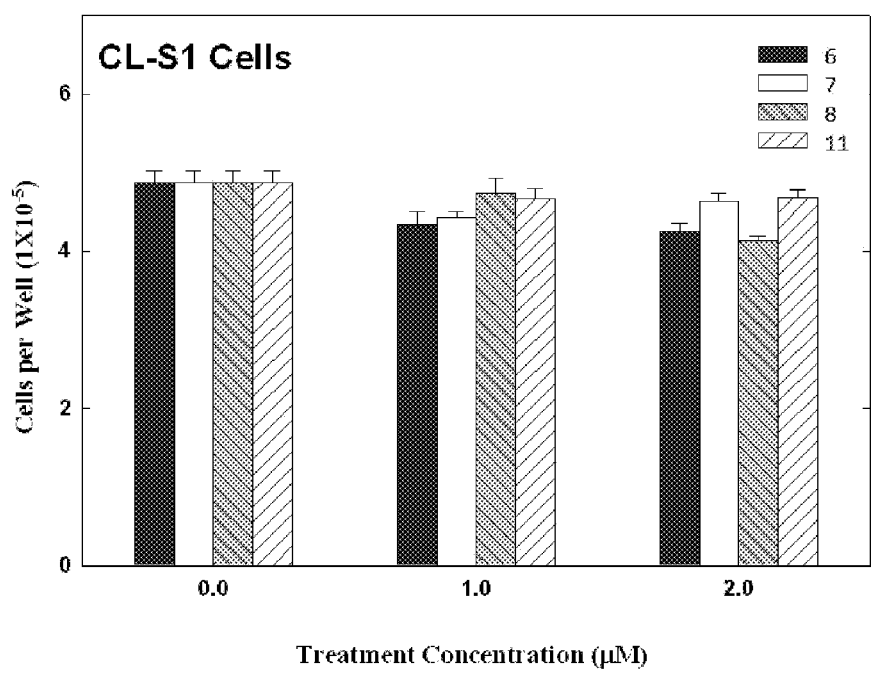
FIG. 20 is a graph of the effects of various treatments of tocotrienol analogues, Compounds 6-8 and 11 on the viability of the normal mammary cells CL-S1.

Compounds 1-8 and 11 were tested for their effects on CL-S1 Cells to evaluate the relative toxicity of those compounds to non-cancerous cells. The normal CL-S1 mammary epithelial cell line is immortal in culture tube, but does not grow in soft agarose or form solid tumors upon transportation back into the mammary pad of syngeneic BALB/c mice. The testing of CL-S1 cells was carried out according to the procedures laid out above for testing of the +SA mammary epithelial cells. FIGS. 17 and 18 compare the anti-proliferative effects of Compounds 1, 2, 3, 4 and 5 on +SA mammary epithelial cells and CL-S1 cells respectively. FIGS. 19 and 20 compare the anti-proliferative effects of Compounds 6, 7, 8, and 11 on +SA mammary epithelial cells and CL-S1 cells respectively.

$IC_{50}$ values were calculated for each of Compounds 1-12 for activity against malignant mice +SA mammary cells. Those $IC_{50}$ values are reflected in Table 2 below.

TABLE 2

| Compound | $IC_{50}$ (μM) |
|---|---|
| 1 | 1.50 |
| 2 | 0.62 |
| 3 | 1.46 |
| 4 | 1.44 |
| 5 | 1.50 |
| 6 | 0.52 |
| 7 | 2.30 |
| 8 | 0.87 |
| 9 | 19.19 |
| 10 | 6.55 |
| 11 | 1.72 |
| 12 | >40 |

Anti-Migratory Assays

Figure 6:
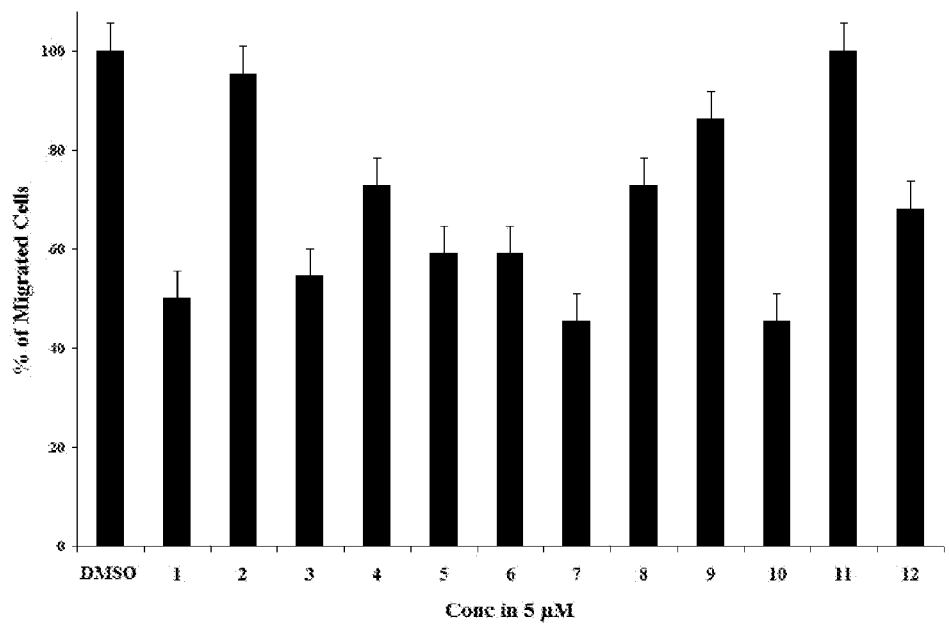
FIG. 6 shows the impact of Compounds 1-12 on MDA-MB-231 tumor cell migration in a wound healing assay.

The highly metastatic human breast cancer MDA-MB-231 cells were cultured in RPMI 1640 medium containing 10 mM HEPES, 4 mM L-glutamine, 10% fetal bovine serum, penicillin (100 IU mL-1), and streptomycin (50 μg mL-1), and grown in a 5% $CO_2$ atmosphere at 37° C. Cells were plated onto sterile 24-well culture plates and allowed to recover for a confluent cell monolayer formed in each well (>95% confluence). Wounds were then inflicted to each cell monolayer using a sterile 200 μL pipette tip. Media were removed, cells monolayers were washed twice with PBS, and then fresh media containing test compounds were added to each well. Test compounds were prepared in DMSO at 5 μM concentration and added to the plates using DMSO as negative control. Tests were preformed in triplicate. The incubation was carried out for 24 hours under serum-starved conditions, after which the media was removed and the cells were fixed and stained using a Romanowski stain sold under the Diff Quick name (Dade Behring Diagnostics, Aguada, Puerto Rico). The number of cells which migrated on the scratched wound were counted under the microscope in three or more randomly selected fields (magnification: 400×). Final results are expressed as mean+/−SEM per 400× field. FIG. 6 shows the effects of Compounds 1-12 and a DMSO control on the migration of MDA-MB-231 tumor cells based on the wound healing assay described above.

Water Solubility

About 5.6 mg of each of α-tocotrienol and Compound 6 were added to 3 mL of phosphate buffer (pH 7.4) in amber vials. Tested solutions were maintained shaking under at 25° C. for 24 h in a constant-temperature water bath. Each solution was then centrifuged at 5,000 rpm for 10 min before collecting samples from the clear supernatant at 0, 1, 2, 4, 6, and 24 h. Each compound concentration in the aspirates was determined by HPLC. The water solubility of the most active ester Compound 6 and its parent α-tocotrienol was investigated in phosphate buffer (pH 7.4, 25° C.). The solubility of α-tocotrienol maleate (Compound 6) was nearly 1000 fold that of its parent α-tocotrienol.

Stability in Phosphate Buffer

The stability of each of α-tocotrienol and Compound 6 was studied at 37° C. in phosphate buffer (pH 7.4). In amber vials, 500 μg/mL of each compound were dissolved in the buffer and the solution was incubated at 37° C. At interval times (0, 0.5, 1, 2, 4, 6, and 24 h), 50 μL it samples were collected and equal volumes of methanol were added to each sample followed by HPLC analysis. The stability of Compound 6 in phosphate buffer (pH 7.4, 37° C.) was also examined. α-Tocotrienol maleate (Compound 6) showed 100% chemical stability relative to the zero time concentration over 24 h. On contrary, α-tocotrienol was highly unstable under the same conditions and started decomposition 1 h after dissolution. α-Tocotrienol was completely undetectable after 24 h, in the buffer solution and other peaks were detected by HPLC with shorter retention times.

Stability in Rat Plasma

The stability of each of α-tocotrienol and Compound 6 was studied at 37° C. in rat plasma. In amber vials, 50 μg/mL of each Compound were dissolved in the plasma. The solution was incubated at 37° C., and at interval times (0, 0.5, 1, 2, 4, 6, and 24 h), 50 μL samples were taken and mixed with 100 μL of methanol followed by centrifugation at 14,000 rpm for 10 min. Each supernatant was analyzed by HPLC. In rat plasma, Compound 6 concentration was 100% stable over the first 3 h. Its concentration then started to decrease at the $4^{th}$ and $5^{th}$ hour to become 81% and 77% of the initial concentration, respectively. After 24 hours, only 43% of the initial concentration of Compound 6 was detectable. The slow rate of hydrolysis of Compound 6 compared to α-tocotrienol may bode well for expected enhanced metabolic stability.

HPLC Analysis of α-tocotrienol and Compound 6

A Shimadzu HPLC system (Columbia, Md.) was used for quantification of α-tocotrienol and Compound 6. This system is composed of SIL 20-AHT autosampler, SPD-20A UV/VIS detector, and LC-20AB pump connected to a Dgu-20A3 degasser. Data acquisition was achieved by LC Solution software version 1.22 SP1 Shimadzu. The following chromatographic conditions were used: Luna 5 μL C18 Column (250× 4.6 mm id; Phenomenex, Torrance, Calif.), flow rate was adjusted to 1.0 mL/min, and λ was set at 295 nm. For α-tocotrienol solubility and stability studies, an isocratic elution with MeOH-EtOH—$CH_3CN$ (40:30:30, v/v/v) as mobile phase for 10 min. α-tocotrienol was eluted at 6.7 min. For the simultaneous separation of α-tocotrienol and Compound 6 the following gradient elution was also used starting with $H_2O$—MeOH—$N(Et)_3$ (10:90:0.05, v/v/v) for 5 min, followed by isocratic MeOH—$N(Et)_3$ (100:0.05, v/v) for another 10 min. The retention times were 4 and 14.1 for Compound 6 and α-tocotrienol, respectively. Standard curves for α-tocotrienol and Compound 6 in MeOH were prepared in the range of 0.4-50 µg/mL and 1-1000 µg/mL, respectively. Each compound was quantified using its calibration curve for compounds peak area versus its concentration.

Experimental Notes

Differences among the various treatment groups in +SA cell cytotoxic studies were determined by analysis of variance (ANOVA) followed by Dunnett's t-test. The difference of $P<0.05$ was considered to be statistically significant as compared with vehicle-treated controls. Linear regression analysis of treatment effects on viable cell number in growth and cytotoxicity studies was used to determine the 50% growth inhibition concentration ($IC_{50}$) for individual treatments.

Tocotrienol isomers were derived from tocotrienol rich fraction of palm oil received from First Tech International Ltd., Hong Kong and was fractionated using silica gel column chromatography with n-hexane/ethylacetate (gradient elution) as a mobile phase to yield pure δ-tocotrienol.

Optical rotations were measured on a Rudolph Research Analytical Autopol III polarimeter. IR spectra were recorded on a Varian 800 FT-IR spectrophotometer. The $^1H$ and $^{13}C$ NMR spectra were recorded in $CDCl_3$, using TMS as an internal standard, on a JEOL Eclipse NMR spectrometer operating at 400 MHz for $^1H$ and 100 MHz for $^{13}C$. Carbon multiplicities were determined by APT experiments with qC=quaternary, CH=methine, CH2=methylene, CH3=methyl carbons. Results for the characterization of Compounds 1-12 are in FIGS. 9-14B. The HREIMS experiments were conducted at Louisiana State University on a 6200-TOF LCMS (Agilent) equipped with multimode source (mixed source that can ionized the compounds alternatively by ESI and APCI). TLC analysis was carried on precoated Si gel 60 $F_{254}$ 500 µm TLC plates (EMD Chemicals), using Ethylacetate/nHexane and Ethylacetate-methanol-water as a mobile phase. For column chromatography, Si gel 60 (particle size mesh 63-200 µm) was used.

Not wishing to be bound by theory, the farnesyl side chain and the chroman ring appear to be pharmacophors for the activity of Compounds 1-12.

Each of Compounds 1-12 showed antiproliferative activity with the exception of Compounds 9, 10, and 12. This is an indication that the presence of free ionizable carboxylic group was significant for antiproliferative activity, and may explain why Compounds 9 and 12 were inactive. The fact that Compound 10 was inactive may shed light on the importance of the unsaturation in the acid. Compounds 2, 6, and 8 exhibited potent anti-proliferative effect against +SA mammary epithelial cells with $IC_{50}$ values of 0.62, 0.51, and 0.86 µM, respectively.

In wound-healing assay, Compounds 1, 3, 5-7, and 10 showed inhibition of nearly 50% of the migrated MDA-MB231 cells at a single dose of 5 µM. Results are slightly different from MTT assay due to the variation in molecular targets in migration versus proliferation.

The results tend to indicate that those compounds that were derived from acyl chlorides with terminal free ionizable groups had higher activities than compounds derived from acyl chlorides without terminal free ionizable groups. Examples of free ionizable groups include alcohols, phenols, and carboxylic acid groups. Embodiments of the invention derived from acylating acids with a pKa of about 2 or less were shown to have antiproliferative and/or anti-migratory effects and embodiments with a pKa of about 3 or less were also shown to have antiproliferative and/or anti-migratory effects. Further, embodiments derived from acylating acids that were olefins or aromatic were shown to have antiproliferative and/or anti-migratory effects.

Not wishing to be bound by theory, Compounds 1-14 may act as prodrugs that slowly release hydrolysis products thereby decreasing the rate of metabolism of the active compounds and enhancing the metabolic stability of tocotrienols. The expected high stability of these compounds may cause improved chemical stability during processing, extended shelf-life during storage, and improved intestinal absorption. Compounds 1-12 may be considered as pro-vitamins or prodrugs of the natural tocotrienol vitamin E members. Further products of the metabolism process may exert potent growth-inhibitory and apoptotic activities in a wide spectrum of in vitro and in vivo cancer models. This potential activity could impact many types of cancer including breast cancer, prostate cancer, neuroblastoma, and mesothelioma.

Not wishing to be bound by theory, several factors may play a role in the observed results. First, the presence of hydrogen bond donating (HBD) and/or accepting (HBA) group may play a role in the activity. Second, an acid that will afford a maximum four-carbon distance between the C-6 oxygen and the HBD and/or HBA group may be preferred for activity. Third, the coexistence of both α,β-unsaturation and HBD and/or HBA group may contribute to high activity. Fourth, the fact that the compounds are redox-silent ester analogues of natural tocotrienols may also contribute to the activity of the compounds. The activity of α-tocotrienol maleate, Compound 6, is of special interest because its parent natural product, α-tocotrienol, was the least active of the natural tocotrienols.

In a method having features of the present invention, any one of the compounds described herein including any pharmaceutically acceptable salts of those compounds could be administered in a therapeutic amount to a mammalian patient in need of the compounds as a method of treating or preventing a form of cancer. In another method having features of the present invention, a mammalian cell is exposed to a therapeutic amount of either one of the several compounds disclosed herein or a pharmaceutically acceptable salt of one of those compounds to either treat or prevent a form of cancer. In separate related embodiments, the mammalian cell is a cancerous cell, the mammalian cell is a human cell, the mammalian cell is breast cancer cell, and the mammalian patient is a human patient. In an embodiment of the invention, the relevant pharmacological composition is the composition with anti-cancerous pharmacological properties that is the product of the in vivo administration of one of the compounds disclosed herein to a mammalian patient.

Many of the compounds tested displayed antiproliferative activity against +SA mammary tumor cells. However, treatment with similar doses of these ester compounds had no effect on the growth or the viability of immortalized normal CL-S1 mammary epithelial cells, suggesting high degree of selectivity toward malignant cells.

Figure 15:
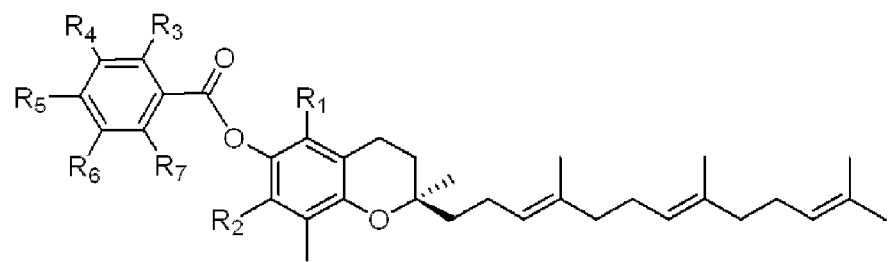
FIG. 15 is a chemical structure drawing representing disclosed compounds.

In a prophetic embodiment of the invention, several additional compounds that share features with one or more of the compounds disclosed above may be characterized generally by the chemical structure of FIG. 15. In that prophetic embodiment $R_1$ is H or $CH_3$; $R_2$ is H or $CH_3$; each of $R_3$, $R_4$, $R_5$, $R_6$, and $R_7$ are selected from COOH, CSOH, $CONH_2$, $SO_3H$, $CSNH_2$, $SO_2H$, OH, and H; and at least one of $R_3$, $R_4$, $R_5$, $R_6$, and $R_7$ is H.

Figure 16:
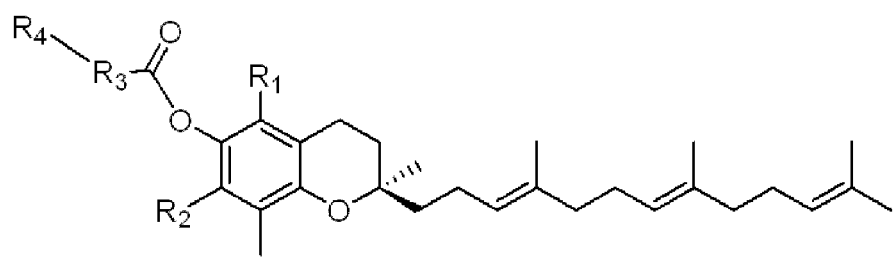
FIG. 16 is a chemical structure drawing representing disclosed compounds.

In a further prophetic embodiment of the invention, several additional compounds that share features with one or more of the compounds disclosed above may be characterized generally by the chemical structure of FIG. 16. In that prophetic embodiment $R_1$ is H or $CH_3$; $R_2$ is H or $CH_3$; $R_3$ is an alkene group having between 2 and 8 carbon atoms; and $R_4$ is selected from COOH, CSOH, $CONH_2$, $SO_3H$, $CSNH_2$, $SO_2H$, and OH.

The compositions disclosed herein may be delivered intravenously, intraperitoneally, subcutaneously, intramuscularly, ocularly, orally, transdermally, topically, by inhalation or by other suitable means.

As used herein, the term "therapeutic amount" indicates an amount which is sufficient to effect beneficial or desired clinical results. Non-limiting examples of these types of results include significant slowing or stopping of the proliferation of cancer cells in a mammal and decreasing the number of live cancer cells in a patient. As used herein, the term "tocotrienol" includes the various isoforms of tocotrienol and compounds which may be derived from one or more of those isoforms and share beneficial therapeutic properties with one or more of the isoforms of tocotrienol. As used herein, the term "pharmaceutically acceptable salt" refers to a salt prepared from any one or multiple non-toxic acid(s) or base(s), including both organic and inorganic acids and bases that are suitable for use in contact with living animal or human tissue without causing adverse physiological responses. As used herein, the term "predominant potency" indicates potency against the +SA mammary epithelial cell lines in antiproliferative assays carried out according to the methods laid out herein utilizing the same weight ratio of compounds as found in the specimen being evaluated and, if practical, using the same concentrations as found in the specimen being evaluated.

Any and all reference to patents, documents and other writings contained herein shall not be construed as an admission as to their status with respect to being or not being prior art. It is understood that the array of features and embodiments taught herein may be combined and rearranged in a large number of additional combinations not directly disclosed, as will be apparent to one having skill in the art and that various embodiments of the invention may have less than all of the benefits and advantages disclosed herein.

There are, of course, other alternate embodiments which are obvious from the foregoing descriptions, which are intended to be included within the scope of the invention, as defined by the following claims.

We claim:

1. A composition comprising a compound selected from the group consisting of:
   4-(((R)-2,5,7,8-tetramethyl-2-((3E,7E)-4,8,12-trimethyltrideca-3,7,11-trienyl)chroman-6-yloxy)carbonyl)isophthalic acid;
   4-(((R)-2,7,8-trimethyl-2-((3E,7E)-4,8,12-trimethyltrideca-3,7,11-trienyl)chroman-6-yloxy)carbonyl)isophthalic acid;
   2-(((R)-2,5,7,8-tetramethyl-2-((3E,7E)-4,8,12-trimethyltrideca-3,7,11-trienyl)chroman-6-yloxy)carbonyl)terephthalic acid;
   2-(((R)-2,7,8-trimethyl-2-((3E,7E)-4,8,12-trimethyltrideca-3,7,11-trienyl)chroman-6-yloxy)carbonyl)terephthalic acid;
   2-(((R)-2,8-dimethyl-2-((3E,7E)-4,8,12-trimethyltrideca-3,7,11-trienyl)chroman-6-yloxy)-carbonyl)terephthalic acid;
   (Z)-4-oxo-4-((R)-2,5,7,8-tetramethyl-2-((3E,7E)-4,8,12-trimethyltrideca-3,7,11-trienyl)chroman-6-yloxy)but-2-enoic acid;
   (Z)-4-oxo-4-((R)-2,7,8-trimethyl-2-((3E,7E)-4,8,12-trimethyltrideca-3,7,11-trienyl)-chroman-6-yloxy)but-2-enoic acid;
   (Z)-4-((R)-2,8-dimethyl-2-((3E,7E)-4,8,12-trimethyl-trideca-3,7,11-trienyl)chroman-6-yloxy)-4-oxobut-2-enoic acid;
   3-Methyl-5-oxo-5-((R)-2,7,8-trimethyl-2-((3E,7E)-4,8,12-trimethyltrideca-3,7,11-trienyl)chroman-6-yloxy)pentanoic acid;
   (R)-2,7,8-trimethyl-2-((3E,7E)-4,8,12-trimethyltrideca-3,7,11-trienyl)chroman-6-yl benzoate;
   5-(((R)-2,7,8-trimethyl-2-((3E,7E)-4,8,12-trimethyltrideca-3,7,11-trienyl)chroman-6-yloxy)carbonyl)benzene-1,2,3-triyl triacetate;
   4-((E)-3-oxo-3-((R)-2,7,8-trimethyl-2-((3E,7E)-4,8,12-trimethyltrideca-3,7,11-trienyl)chroman-6-yloxy)prop-1-enyl)-1,2-phenylene diacetate;
   (R)-2,7,8-trimethyl-2-((3E,7E)-4,8,12-trimethyltrideca-3,7,11-trienyl)chroman-6-yl 3,4,5-trihydroxybenzoate; and
   (E)-((R)-2,7,8-trimethyl-2-((3E,7E)-4,8,12-trimethyltrideca-3,7,11-trienyl)chroman-6-yl) 3-(3,4-dihydroxyphenyl)acrylate.

2. The composition of claim 1 wherein the compound is 4-(((R)-2,5,7,8-tetramethyl-2-((3E,7E)-4,8,12-trimethyltrideca-3,7,11-trienyl)chroman-6-yloxy)carbonyl)isophthalic acid.

3. The composition of claim 1 wherein the compound is 4-(((R)-2,7,8-trimethyl-2-((3E,7E)-4,8,12-trimethyltrideca-3,7,11-trienyl)chroman-6-yloxy)carbonyl)isophthalic acid.

4. The composition of claim 1 wherein the compound is 2-(((R)-2,5,7,8-tetramethyl-2-((3E,7E)-4,8,12-trimethyltrideca-3,7,11-trienyl)chroman-6-yloxy)carbonyl)terephthalic acid.

5. The composition of claim 1 wherein the compound is 2-(((R)-2,7,8-trimethyl-2-((3E,7E)-4,8,12-trimethyltrideca-3,7,11-trienyl)chroman-6-yloxy)carbonyl)terephthalic acid.

6. The composition of claim 1 wherein the compound is 2-(((R)-2,8-dimethyl-2-((3E,7E)-4,8,12-trimethyltrideca-3,7,11-trienyl)chroman-6-yloxy)-carbonyl)terephthalic acid.

7. The composition of claim 1 wherein the compound is (Z)-4-oxo-4-((R)-2,5,7,8-tetramethyl-2-((3E,7E)-4,8,12-trimethyltrideca-3,7,11-trienyl)chroman-6-yloxy)but-2-enoic acid.

8. The composition of claim 1 wherein the compound is (Z)-4-oxo-4-((R)-2,7,8-trimethyl-2-((3E,7E)-4,8,12-trimethyltrideca-3,7,11-trienyl)chroman-6-yloxy)but-2-enoic acid.

9. The composition of claim 1 wherein the compound is (Z)-4-((R)-2,8-dimethyl-2-((3E,7E)-4,8,12-trimethyltrideca-3,7,11-trienyl)chroman-6-yloxy)-4-oxobut-2-enoic acid.

10. The composition of claim 1 wherein the compound is 3-Methyl-5-oxo-5-((R)-2,7,8-trimethyl-2-((3E,7E)-4,8,12-trimethyltrideca-3,7,11-trienyl)chroman-6-yloxy)pentanoic acid.

11. The composition of claim 1 wherein the compound is (R)-2,7,8-trimethyl-2-((3E,7E)-4,8,12-trimethyltrideca-3,7,11-trienyl)chroman-6-yl benzoate.

12. The composition of claim 1 wherein the compound is 5-(((R)-2,7,8-trimethyl-2-((3E,7E)-4,8,12-trimethyltrideca-3,7,11-trienyl)chroman-6-yloxy)carbonyl)benzene-1,2,3-triyl triacetate.

13. The composition of claim 1 wherein the compound is 4-((E)-3-oxo-3-((R)-2,7,8-trimethyl-2-((3E,7E)-4,8,12-trimethyltrideca-3,7,11-trienyl)chroman-6-yloxy)prop-1-enyl)-1,2-phenylene diacetate.

14. The composition of claim 1 wherein the compound is (R)-2,7,8-trimethyl-2-((3E,7E)-4,8,12-trimethyltrideca-3,7,11-trienyl)chroman-6-yl 3,4,5-trihydroxybenzoate.

15. The composition of claim 1 wherein the compound is (E)-((R)-2,7,8-trimethyl-2-((3E,7E)-4,8,12-trimethyltrideca-3,7,11-trienyl)chroman-6-yl) 3-(3,4-dihydroxyphenyl)acrylate.

16. A composition comprising a compound of the general formula (I)

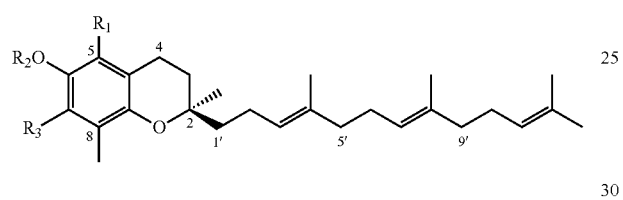

(I)

wherein $R_1$ is selected from H and $CH_3$;
wherein $R_3$ is selected from H and $CH_3$; and
wherein $R_2$ is a functional group selected from:

a
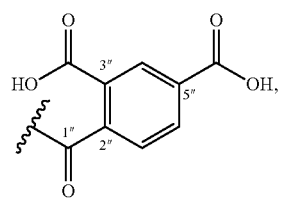

b
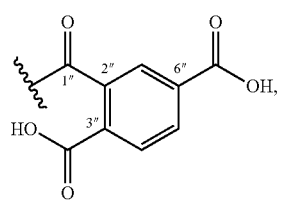

c
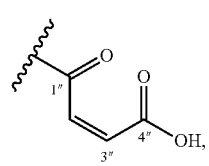

d
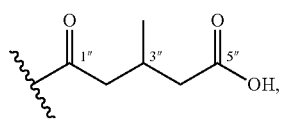

e
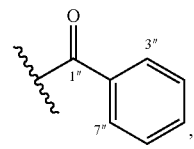

f
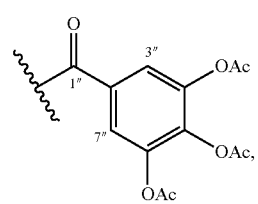

g
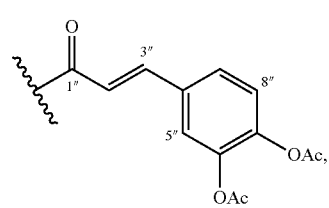

h
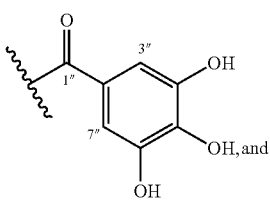

i
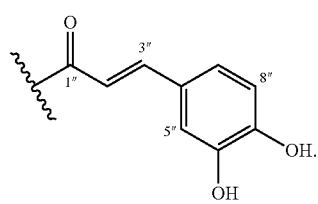

17. The composition of claim 16 wherein the functional group is:

a
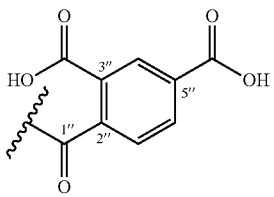

and $R_3$ is $CH_3$.

18. The composition of claim 16 wherein the functional group is:

c
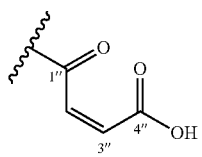

and $R_1$ is $CH_3$.

19. The composition of claim 16 wherein the functional group is:

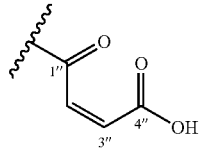           c and R₁ is H.

20. The composition of claim 16 wherein the functional group is:

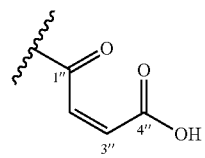           c and R₃ is CH₃.

21. The composition of claim 17 wherein the functional group is:

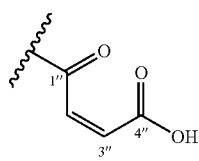           c and R₃ is H.

22. The composition of claim 16 wherein R₁ is H and R₃ is CH₃.

23. The composition of claim 16 wherein R₂ is selected from

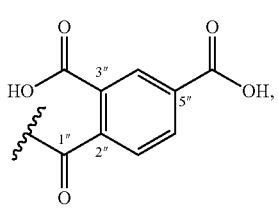           a

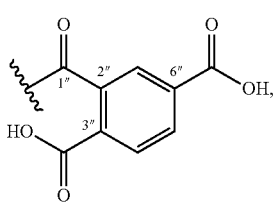           b

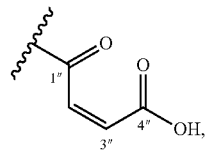           c

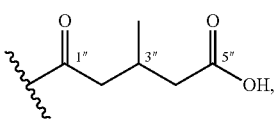           d

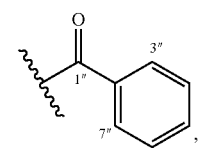           e

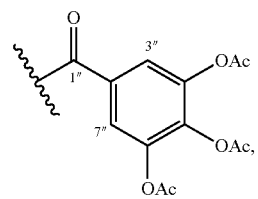           f

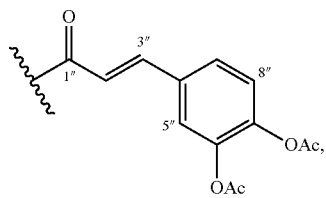          g

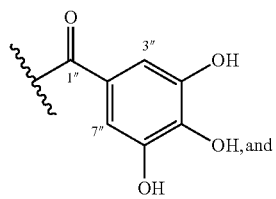          h

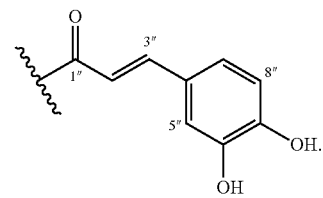          i

24. A treatment method comprising exposing a mammalian cell to either a first amount of a compound or a second amount of a pharmaceutically acceptable salt of said compound, wherein said compound is selected from:

4-(((R)-2,5,7,8-tetramethyl-2-((3E,7E)-4,8,12-trimethyl-trideca-3,7,11-trienyl)chroman-6-yloxy)carbonyl) isophthalic acid;

4-(((R)-2,7,8-trimethyl-2-((3E,7E)-4,8,12-trimethyl-trideca-3,7,11-trienyl)chroman-6-yloxy)carbonyl) isophthalic acid;

2-(((R)-2,5,7,8-tetramethyl-2-((3E,7E)-4,8,12-trimethyl-trideca-3,7,11-trienyl)chroman-6-yloxy)carbonyl) terephthalic acid;

2-(((R)-2,7,8-trimethyl-2-((3E,7E)-4,8,12-trimethyltrideca-3,7,11-trienyl)chroman-6-yloxy)carbonyl)terephthalic acid;

2-(((R)-2,8-dimethyl-2-((3E,7E)-4,8,12-trimethyltrideca-3,7,11-trienyl)chroman-6-yloxy)-carbonyl)terephthalic acid;

(Z)-4-oxo-4-((R)-2,5,7,8-tetramethyl-2-((3E,7E)-4,8,12-trimethyltrideca-3,7,11-trienyl)chroman-6-yloxy)but-2-enoic acid;

(Z)-4-oxo-4-((R)-2,7,8-trimethyl-2-((3E,7E)-4,8,12-trimethyltrideca-3,7,11-trienyl)-chroman-6-yloxy)but-2-enoic acid;

(Z)-4-((R)-2,8-dimethyl-2-((3E,7E)-4,8,12-trimethyltrideca-3,7,11-trienyl)chroman-6-yloxy)-4-oxobut-2-enoic acid;

3-Methyl-5-oxo-5-((R)-2,7,8-trimethyl-2-((3E,7E)-4,8,12-trimethyltrideca-3,7,11-trienyl)chroman-6-yloxy) pentanoic acid;

(R)-2,7,8-trimethyl-2-((3E,7E)-4,8,12-trimethyltrideca-3,7,11-trienyl)chroman-6-yl benzoate;

5-(((R)-2,7,8-trimethyl-2-((3E,7E)-4,8,12-trimethyltrideca-3,7,11-trienyl)chroman-6-yloxy)carbonyl)benzene-1,2,3-triyl triacetate;

4-((E)-3-oxo-3-((R)-2,7,8-trimethyl-2-((3E,7E)-4,8,12-trimethyltrideca-3,7,11-trienyl)chroman-6-yloxy)prop-1-enyl)-1,2-phenylene diacetate;

(R)-2,7,8-trimethyl-2-((3E,7E)-4,8,12-trimethyltrideca-3,7,11-trienyl)chroman-6-yl 3,4,5-trihydroxybenzoate; and (E)-((R)-2,7,8-trimethyl-2-((3E,7E)-4,8,12-trimethyltrideca-3,7,11-trienyl)chroman-6-yl) 3-(3,4-dihydroxyphenyl)acrylate.

25. The method of claim 24 wherein the compound is 4-(((R)-2,7,8-trimethyl-2-((3E,7E)-4,8,12-trimethyltrideca-3,7,11-trienyl)chroman-6-yloxy)carbonyl)isophthalic acid.

26. The method of claim 24 wherein the compound is (Z)-4-oxo-4-((R)-2,5,7,8-tetramethyl-2-((3E,7E)-4,8,12-trimethyltrideca-3,7,11-trienyl)chroman-6-yloxy)but-2-enoic acid.

27. The method of claim 24 wherein the compound is (Z)-4-((R)-2,8-dimethyl-2-((3E,7E)-4,8,12-trimethyltrideca-3,7,11-trienyl)chroman-6-yloxy)-4-oxobut-2-enoic acid.

28. The composition of claim 1 wherein the compound has the predominant potency in the composition.

* * * * *